United States Patent
Izatt et al.

(10) Patent No.: US 7,362,444 B2
(45) Date of Patent: *Apr. 22, 2008

(54) INTERFEROMETERS FOR OPTICAL COHERENCE DOMAIN REFLECTOMETRY

(75) Inventors: Joseph A. Izatt, Pepper Pike, OH (US); Andrew M. Rollins, Bedford, OH (US)

(73) Assignee: Case Western Reserve University, Cleveland, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 11/470,079

(22) Filed: Sep. 5, 2006

(65) Prior Publication Data

US 2007/0024868 A1 Feb. 1, 2007

Related U.S. Application Data

(60) Continuation of application No. 10/646,202, filed on Aug. 22, 2003, now Pat. No. 7,102,756, which is a division of application No. 09/393,761, filed on Sep. 10, 1999, now Pat. No. 6,657,727.

(60) Provisional application No. 60/100,032, filed on Sep. 11, 1998.

(51) Int. Cl.
*G01B 11/02* (2006.01)
*G01B 9/02* (2006.01)

(52) U.S. Cl. ................................ 356/479; 356/497
(58) Field of Classification Search ................ 356/477, 356/479, 497; 385/12

See application file for complete search history.

(56) References Cited

U.S. PATENT DOCUMENTS

| 4,063,549 A | 12/1977 | Beretsky et al. |
| 5,158,090 A | 10/1992 | Waldman et al. |
| 5,200,819 A | 4/1993 | Nudelman et al. |

(Continued)

FOREIGN PATENT DOCUMENTS

WO 97/32182 4/1997

(Continued)

OTHER PUBLICATIONS

Michael R. Hee, Joseph A. Izatt, Joseph M. Jacobson and James G. Fujimoto; "Femtosecond Transillumination Optical Coherence Tomography"; Jun. 15, 1993, vol. 18, No. 12 *Optics Letters*, pp. 950-952.

(Continued)

*Primary Examiner*—Gregory J. Toatley, Jr.
*Assistant Examiner*—Patrick Connolly

(57) ABSTRACT

An interferometer system includes an optical radiation source, an optical circulator connected between the optical radiation source and a sample location for transmitting optical radiation from the optical radiation source to the sample location, an output of the optical circulator connected to direct optical radiation to an optical detector. Various embodiments of such a system are possible. A method of performing OCDR or OCT imaging of a sample which involves the steps of: (a) producing low coherence optical radiation; (b) directing at least some of the low coherence optical radiation through an optical circulator to the sample; (c) reflecting at least some of the low coherence optical radiation off of the sample; and (d) detecting at least some of the reflected low coherence optical radiation and producing an electrical signal corresponding thereto.

20 Claims, 11 Drawing Sheets

U.S. PATENT DOCUMENTS

| | | | |
|---|---|---|---|
| 5,353,802 A | 10/1994 | Ollmar | |
| 5,459,570 A | 10/1995 | Swanson et al. | |
| 5,491,524 A | 2/1996 | Hellmuth et al. | |
| 5,493,109 A | 2/1996 | Wei et al. | |
| 5,501,226 A | 3/1996 | Petersen et al. | |
| 5,535,000 A | 7/1996 | Shirasaki | |
| 5,549,114 A | 8/1996 | Petersen et al. | |
| 5,565,986 A | 10/1996 | Knüttel | |
| 5,644,642 A | 7/1997 | Kirschbaum | |
| 5,894,531 A | 4/1999 | Alcoz | |
| 5,956,355 A | 9/1999 | Swanson et al. | |
| 6,088,491 A | 7/2000 | Sorin et al. | |
| 6,134,003 A * | 10/2000 | Tearney et al. | 356/479 |
| 6,175,669 B1 * | 1/2001 | Colston et al. | 385/12 |
| 6,201,608 B1 * | 3/2001 | Mandella et al. | 356/491 |
| 6,233,055 B1 * | 5/2001 | Mandella et al. | 356/479 |
| 6,252,666 B1 * | 6/2001 | Mandella et al. | 356/479 |
| 6,307,633 B1 * | 10/2001 | Mandella et al. | 356/479 |
| 6,384,915 B1 * | 5/2002 | Everett et al. | 356/336 |
| 6,501,551 B1 * | 12/2002 | Tearney et al. | 356/477 |

FOREIGN PATENT DOCUMENTS

| | | |
|---|---|---|
| WO | 00/69333 A | 11/2000 |

OTHER PUBLICATIONS

Everett M.J. et al.; "Non-invasive Diagnosis of Early Caries with Polarization Sensitive Optical Coherence Tomography", Proceedings of the SPIE, SPIE, Bellingham, VA, us, vol. 3593, Jan. 24, 1999, pp. 177-182, XP000931184, Chapter 3, pp. 178-179, Figure 1.

Podoleanu A.G. et al.; "Simultanious En-Face Imaging of Two Layers in the Human Retina by Low-Coherence Reflectometry", Optics Letters, Optical Society of America, Washington, US. vol. 22, No. 13, Jul. 1, 1997, pp. 1039-1041, XP000658709.

Podoleanu A.G. et al.; "Simultaneous Low coherence Interferometry Imaging at Two Depths Using An Integrated Optic Modulator", Optics Communications, North-Holland Publishing Co., Amsterdam, NL, vol. 191, No. 1-2, May 1, 2001, pp. 21-30, XP004234990.

Boer, De J.F. et al.; "Polarization Effects in Optical Coherence Tomography of Various Biological Tissues", IEEE Journal of Selected Topics in Quantum Electronics, IEEE Service Center, US., vol. 5, No. 4, Jul. 1999, pp. 1200-1203, XP00893469, Chapter III, pp. 1200-1201, Figure 1.

Deconvolution and Enhancement of Optical Coherence Tomograms, J.M. Schmitt et al., SPIE, vol. 2981, pp. 46-57, 64-75 (Feb. 1997).

Phase-Only Blind Deconvolution Using Bicepstrum Iterative Reconstruction Algorithm (BIRA), R.S. Holambe et al., *IEEE Transactions on Signal Processing*, vol. 44, No. 9, pp. 2356-2359 (Sep. 1996).

In Vivo Endoscopic OCT Imaging of Precancer and Cancer Sates of Human Mucosa, A.M. Sergeev et al., *Optics Express*, vol. 1, No. 13, pp. 432-440 (Dec. 1997).

Comparison of Some Non-Adaptive Deconvolution Techniques for Resolution Enhancement of Ultrasonic Data, G. Hayward et al., *Ultrasonics*, vol. 27, pp. 155-164 (May 1989).

Supperresolution Three-Dimensional Images of Fluorescence in Cells with Minimal Light Exposure, W.A. Carrington et al., *Science*, vol. 268, pp. 1483-1487 (Jun. 1995).

Optical Coherence Tomography of Scattering Media Using Frequency Modulated Continuous Wave Techniques with Tunable Near-Infrared Laser, U. Haberland et al., SPIE, vol. 2981 (Proceedings of Coherence Domain Optical Methods in Biomedical Science and Clinical Applications), pp. 20-28 (Feb. 1997).

Constrained Iterative Restoration Algorithms, R.W. Schafer et al., *Proceedings of the IEEE*, vol. 69, No. 4, pp. 432-450 (Apr. 1981).

Blindness Limitations in Optical Coherence Domain Reflectometry, S.R. Chinn et al., *Electronics Letters*, vol. 23, pp. 2025-2027 (Nov. 1993).

Optical Coherence Tomography, D. Huang et al., *Science*, vol. 254, pp. 1178-1181 (Nov. 1991).

Systems and Transforms with Applications in Optics, A. Papoulis, pp. 254-293, McGraw-Hill Book Co. (1968).

Maximum-Likelihood Deconvolution, A Journey into Model-Based Signal Processing, J.M. Mendel, pp. 1-77, Springer-Verlag New York, Inc. (1990).

Fundamentals of Statistical Signal Processing: *Estimation Theory*, S.M. Kay, pp. 364-371 (1993).

Low-coherence Optical Tomography in Turbid Tissue: Theoretical Analysis, Y. Pan et al., *Applied Optics*, vol. 34, No. 28, pp. 6564-6574 (Oct. 1995).

Micrometer-Scale Resolution Imaging of the Anterior Eye in Vivo with Optical Coherence Tomography, J.A. Izatt et al., *Arch Ophthalmol*, vol. 112, pp. 1584-1589 (Dec. 1994).

Optical Coherence-Domain Reflectometry: A New Optical Evaluation Technique, R.C. Youngquist et al., *Optics Letters*, vol. 12, No. 3, pp. 158-160 (1987).

Spatially Coherent White-light Interferometer Based on a Point Fluorescent Source, H. Liu et al., *Optics Letters*, vol. 18, No. 9, pp. 678-680 (May 1993).

High-resolution Reflectometry in Biological Tissues, X. Clivaz et al., *Optics Letters*, vol. 17, No. 1, pp. 4-6 (Jan. 1992).

Optical Low Coherence Reflectometry with 1.9 μm Spatial Resolution, X. Clivaz et al., *Electronics Letters*, vol. 28, No. 16, pp. 1553-1555 (Jul. 1992).

High-speed Optical Coherence Domain Reflectometry, E.A. Swanson et al., *Optics Letters*, vol. 17, No. 2, pp. 151-153 (Jan. 1992).

Optical-Coherence Tomography of a Dense Tissue: Statistics of Attenuation and Backscattering, J.M. Schmitt et al., *Phys. Med. Biol*, 39, pp. 1705-1720 (1994).

High-Resolution optical coherence tomographic Imaging Using a Mode-locked Tl:Al$_2$O$_3$ Laser Source, B. Bouma et al., *Optics Letters*, vol. 20, No. 13, pp. 1486-1488 (Jul. 1995).

Self-phase-modulated Kerr-lens Mode-locked Cr: forsterite Laser Source for Optical Coherence Tomography, B.E. Bouma et al., *Optics Letters*, vol. 21, No. 22, pp. 1839-1841 (Nov. 1996).

High-speed Phase- and Group-delay Scanning with a Grating-based Phase Control Delay Line, G.J. Tearney et al., *Optics Letters*, vol. 22, No. 23, pp. 1811-1813 (Dec. 1997).

Optical Coherence Tomography Using a Frequency-Tunable Optical Source, S.R. Chinn et al., *Optics Letters*, vol. 22, No. 5, pp. 340-342 (Mar. 1997).

Tissue Optics, D.A. Benaron et al., *Science*, vol. 276, pp. 2002-2003 (Jun. 1997).

In Vivo Endoscopic Optical Biopsy with Optical Coherence Tomography, G.J. Tearney, *Science*, No. 276, pp. 2037-2039 (Jun. 1997).

Fast Algorithms for $1_p$ Deconvulution, R. Yarlagadda et al., *IEEE Transactions on Acoustics, Speech, and Signal Processing*, vol. ASSP-33, No. 1, pp. 174-182 (Feb. 1985).

The Design of High-Resolution Digital Filters, S. Treitel et al., *IEEE Transactions on Geoscience Electronics*, vol. GE-4, No. 1, pp. 25-38 (Jun. 1966).

A Comprehensive Solution to the Linear Deconvolution Problem, D.W. Oldenburg, *Geophys. J.R. astr. Soc.*, 65, pp. 331-357 (1981).

Digital Processing of Ultrasonic Data by Deconvolution, E.E. Hundt et al., *IEEE Transactions on Sonics and Ultrasonics*, vol. SU-27, No. 5, pp. 249-252 (Sep. 1980).

Sternad: Wiener Filter Design Using Polynomial Equations, A. Ahlén et al., *IEEE Transactions on Signal Processing*, vol. 39, No. 11, pp. 2387-2399 (pp. 2388-2389 missing) (Nov. 1991).

Maximum Likelihood Estimation of the Attenuated Ultrasound Pulse, K.B. Rasmussen, *IEEE Transactions on Signal Processing*, vol. 42, No. 1, pp. 220-222 (Jan. 1994).

Deconvolution of In Vivo Ultrasound Images, J.A.. Jensen, 1990 Ultrasonics Symposium, pp. 1581-1587 (1990).

An Iterative Restoration Technique, S. Singh, et al., *Signal Processing*, 11, pp. 1-11 (1986).

Video Rate Optical Coherence Tomography, A.M. Rollins et al., Advances in Optical Imaging & Photon Migration, Trends in Optics & Photonics, Optical Society of America, from the topical meeting Mar. 8-11, 1998, Orlando, Florida (1998).

Micron-Resolution Biomedical Imaging with Optical Coherence Tomography, J. Izatt et al., *Optics & Photonics News* (Oct. 1993).

Characterization of Fluid Flow Velocity by Optical Doppler Tomography, X. Wang et al., *Optics Letters*, vol. 20, No. 11 (Jun. 1, 1995).

Optical Doppler Tomography Imaging of Fluid Flow Velocity in Highly Scattered Media, Z. Chen et al., *Optics Letters*, vol. 22, No. 1, pp. 64-66 (Jan. 1, 1997).

Distributed Laser Doppler Velocimeter, V. Gusmeroli et al., *Optics Letters*, vol. 16, No. 17 (Sep. 1, 1991).

Noninvasive Imaging of In Vivo Blood Flow Velocity Using Optical Doppler Tomography, Z. Chen et al., *Optics Letters*, vol. 22, No. 14 (Jul. 15, 1997).

*Cleo '97: Summaries of papers presented at the Conference on Lasers and Electro-Optics*, 1997 OSA Technical Digest Series, vol. 11, Conference Edition, pp. 211-212, Baltimore, MD (May 18-23, 1997).

Real-Time Two Dimensional Blood Flow Imaging using an Autocorrelation Technique, C. Kasai et al., *IEEE Transactions on Sonics and Ultrasonics*, vol. SU-32, No. 3 (May 1985).

*Doppler Ultrasound: Physics, Instrumentation, and Clinical Applications*, chapter 6: Basic Doppler Electronics and Signal Processing, D.H. Evans et al., pp. 84-107, John Wiley & Sons, New York (1989).

*Vascular Diagnosis, 4th Ed.*, Chapter 12: Principles and pitfalls of real-time color flow imaging, F.W. Kremkau, pp. 90-105, Mosby Year-Book, Inc., Missouri (1993).

*Vascular Diagnosis, 4th Ed.*, Chapter 11: Pulsed Doppler Ultrasound for Blood Velocity Measurements, K.W. Beach at al., pp. 83-89, Mosby Year-Book, Inc., Missouri (1993).

Velocity-Estimation Accuracy and Frame-Rate Limitations in Color Doppler Optical Coherence Tomography, M.D. Kulkarni et al., *Optics Letters*, vol. 23, No. 13 (Jul. 1, 1989).

Investigating Laser-Blood Vessel Interaction with Color Doppler Optical Coherence Tomography, J.K. Barton et al., *Progress in Biomedical Optics: Proceedings of Coherence Domain Optical Methods in Biomedical Science and Clinical Applications II*, San Jose, CA *SPIE*, vol. 3251 (Jan. 27-28, 1998).

Diagnostic Blood Flow Monitoring during Therapeutic Interventions using Color Doppler Optical Coherence Tomography, S. Yazdanfar et al., *Progress in Biomedical Optics: Proceedings of Coherence Domain Optical Methods in Biomedical Science and Clinical Applications II*, San Jose, CA, *SPIE*, vol. 3251 (Jan. 27-28, 1998).

High Resolution Imaging of In Vivo Cardiac Dynamics using Color Doppler Optical Coherence Tomography, S. Yazdanfar et al., *Optics Express*, vol. 1, No. 13 (Dec. 22, 1997).

Detection of Gastrointestinal Cancer by Elastic Scattering and Absorption Spectroscopies with the Los Alamos Optical Biopsy System, *Progress in Biomedical Optics: Proceedings of Advances in Laser and Light Spectroscopy to Diagnose Cancer and Other Diseases II*, San Jose, CA (Feb. 7-8, 1995).

Rapid Near-Infrared Raman Spectroscopy of Human Tissue with a Spectrograph and CCD Detector, J.J. Baraga, *Applied Spectroscopy*, vol. 46, No. 2 (1992).

Theoretical and Experimental Investigations of Elastic Scattering Spectroscopy as a Potential Diagnostic for Tissue Pathologies, J. Boyer et al., *OSA Proceedings on Advances in Optical Imagine and Photon Migration*, vol. 21, Orlando, FL (Mar. 21-23, 1994).

Notification of Transmittal of the International Search Report or the Declaration in PCT Application Serial No. US99/20670, dated Feb. 7, 2000.

In Vivo Bidirectional Color Doppler Flow Imaging of Picoliter Blood Volumes using Optical Coherence Tomography, J.A. Izatt et al., *Optics Letters*, vol. 22, No. 18 (Sep. 15, 1997).

In Vivo Doppler Flow Imaging of Picoliter Blood Volumes using Optical Coherence Tomography, J.A. Izatt et al., *Cleo '97: Summaries of papers presented at the Conference on Lasers and Electro-Optics, 1997 OSA Technical Digest Series*, vol. 11, Conference Edition, Baltimore, MD (May 18-23, 1997).

Optical Coherence Tomography for Biodiagnostics, J.A. Izatt et al., *Optics & Photonicvs News* (May 1997).

Doppler Flow Imaging Using Optical Coherence Tomography, J.A. Izatt et al., *Cleo '96 Postdeadline Papers, Conference on Lasers and Electro-Optics*, Anaheim, CA (Jun. 2-7, 1996).

Model for Laser Doppler Measurements of Blood Flow in Tissue, R. Bonner et al., *Applied Optics*, vol. 20, No. 12 (Jun. 15, 1981).

Time-resolved Studies of Stimulated Emission from Colloidal Dye Solutions, M. Siddique et al., *Optics Letters*, vol. 21, No. 7 (Apr. 1, 1996).

*Laser Action in Polymeric Gain Media Containing Scattering Particles*, R.M. Balachandran et al., *Applied Optics*, vol. 35, No. 4 (Feb. 1, 1996).

Laser Action in Strongly Scattering Media, N.M. Lawandy et al., *Nature*, vol. 368 (Mar. 31, 1994).

Three Ways to Implement Interferencial Techniques: Application to Measurements of Chromatic Dispersion, Birefringence, and Non-linear Susceptibilities, P.L. Francois et al., *Journal of Lightwave Technology*, vol. 7, No. 3 (Mar. 1989).

Precise Characterization of the Raman nonlinearity in Benzene using Nonlinear Interferometry, A. Owyoung et al., *Journal of Applied Physics*, vol. 48, No. 2 (Feb. 1977).

Simultaneous Measurement of Dispersion, Spectrum, and Distance with a Fourier Transform Spectrometer, T. Hellmuth et al., *Journal of Biomedical Optics*, vol. 3, No. 1 (Jan. 1998).

Ultrasonic Tissue Characterization of Uveal Melanoma and Prediction of Patient Survival After Enucleation and Brachytherapy, D.J. Coleman et al., *American Journal of Ophthalmology*, 112; pp. 682-688 (Dec. 1991).

Correlations of Acoustic Tissue Typing of Malignant Melanoma and Histopathologic Features as a Predictor of Death, D.J. Coleman et al., *American Journal of Ophthalmology*, pp. 110; 380-388 (Oct. 1990).

Theoretical Framework for Spectrum Analysis in Ultrasonic Tissue Characterization, F.L. Lizzi et al., *J. Acoust, Soc. Am.*, pp. 73(4) (Apr. 1983).

Spectroscopic Optical Coherence Tomography, M.D. Kulkarni et al., Conference on Lasers and Electro-Optics, vol. 9 1996 Technical Digest Series Conference Edition (Jun. 2-7, 1996).

Diagnostic Spectrum Analysis in Ophthalmology: A Physical Perspective, E.J. Feleppa, *Ultrasound in Med. & Biol*, vol. 12, No. 8 (1986).

Noninvasive Identification of Bladder Cancer with Sub-surface Backscattered Light, I.J. Bigio et al., *Progress in Biomedical Optics: Proceedings of Advances in Laser and Light Spectroscopy to Diagnose Cancer and Other Diseases*, Los Angeles, CA (Jan. 23-24, 1994).

\* cited by examiner

BEAMSPLITTER/FIBER COUPLER

OPTICAL CIRCULATOR

OPTICAL CIRCULATOR IMPLEMENTATION USING A POLARIZED BEAMSPLITTER (PBS) AND FARADAY ROTATOR (FR)

MACH-ZENDER (TRANSMISSIVE) OCDR/OCT (EMBODIMENT 6)

(EMBODIMENT 7)

(EMBODIMENT 8)

INTERFEROMETERS FOR OPTICAL COHERENCE DOMAIN REFLECTOMETRY

CROSS-REFERENCE TO RELATED APPLICATIONS

This application is a continuation of U.S. application Ser. No. 10/646,202, filed Aug. 22, 2003, now U.S. Pat. No. 7,102,756, which is a divisional of U.S. application Ser. No. 09/393,761, filed Sep. 10, 1999, now U.S. Pat. No. 6,657,727, which claims the benefit of U.S. Provisional Application No. 60/100,032, filed Sep. 11, 1998, the entire disclosures of which are incorporated by reference.

FUNDING

This invention was made with government support under NSF Grant No. BES9624617. The government has certain rights in the invention.

BACKGROUND OF THE INVENTION

Optical Coherence Tomography (OCT) is a novel imaging technique which allows for noninvasive cross-sectional imaging in scattering or cloudy media with high spatial resolution and high dynamic range. OCT is a two-dimensional extension of Optical Coherence-Domain Reflectometry (OCDR) which is also commonly referred to as Optical Low Coherence Reflectometry (OLCR), in which a low temporal coherence light source is employed to obtain precise localization of reflections internal to a probed structure along the optic axis. The one-dimensional ranging technique of OCDR/OLCR has previously been utilized for characterization of bulk-, integrated-, and fiber-optic structures, as well as biological tissues. In OCT, this technique is extended to provide for scanning of the probe beam in a direction perpendicular to the optic axis, building up a two-dimensional data set comprising a cross-sectional image of internal tissue backscatter.

Ophthalmic Applications of OCT

OCT has previously been applied to imaging of biological tissues in vivo and in vitro, although the majority of initial biomedical imaging studies concentrated on transparent structures such as the eye. Initial ophthalmic imaging studies demonstrated significant potential for OCT imaging in routine examination of normal and abnormal ocular structures, including imaging of the cornea, iris, and other structures of the anterior eye; the lens and lens capsule; and numerous structures in the posterior eye, including the neurosensory retina, retinal nerve fiber layer, retinal pigment epithelium, and choroid. In OCT examination of the retina, initial in vivo clinical studies have demonstrated its utility in aiding diagnosis in a variety of vitreoretinal diseases, including macular hole, macular degeneration, detached retina, and glaucoma. Clinical trials of OCT imaging for ophthalmic applications are currently under way at several centers, and a commercial ophthalmic OCT scanner is available from Humphrey Systems of Dublin, Calif.

OCT Imaging in Highly Scattering Media

Several recent publications have demonstrated the potential applications of OCT in highly scattering media for the measurement of tissue optical properties and imaging. Optical imaging in scattering media such as biological tissue is in general a very difficult problem, particularly for techniques such as OCT which depend primarily upon unscattered or singly-scattered light for image formation. It has been observed in preliminary studies and theoretical treatments that this singly-scattered gating requirement practically limits OCT imaging to a useful penetration depth of a few millimeters at best in nontransparent human tissues. Nonetheless, several authors have identified diagnostic scenarios in which a technique for improved, non-invasive 10-20-micron scale optical imaging near tissue surfaces has significant potential for clinical utility. These include applications of OCT imaging in skin, teeth, vascular tissues, and gastrointestinal mucosa. The latter two examples are significant since with its fiber optic implementation, OCT is readily adaptable to minimally invasive diagnostic modalities such as catheterization or endoscopy. OCT system implementations featuring the high-speed imaging acquisition necessary for in vivo application and catheter/endoscopic delivery have been reported. The application of OCT to biomedical imaging provides the potential for sub-surface tissue characterization with sufficient resolution to provide microscopic morphological information relevant to pathological diagnosis without the need for biopsy.

OCT Imaging in Industrial Processing

Recent publications have also illustrated the potential applications of OCT for imaging in cloudy or turbid non-biological media in industrial processing in the manufacturing industry. OCT imaging may be useful for on-line process control or product testing and evaluation. Initial experiments have demonstrated OCT imaging in ceramic and other highly scattering materials, as well as for the characterization of the surface topology of opaque industrial materials such as metals (i.e., ball bearings).

OCT Qualitative Technical Description

Optical coherence tomography performs micron-scale topographic imaging of internal tissue microstructure using a combination of the principles of low-coherence interferometry and confocal microscopy. Reference is made to FIG. 1 illustrating an exemplary OCT system 10 in which the tissue to be examined is placed in the sample arm 12 of a Michelson interferometer illuminated by a broadband light source 16. Due to the limited coherence length of the source (typically 10-15 microns), light returning from the reference arm 18 and light backscattered by internal sample reflections interferes constructively or destructively only when the interferometer arm optical path lengths are matched to within the source coherence length. Scanning the reference arm 18 length through a position corresponding to the depth of a reflecting site within the sample generates a localized interference pattern, which is recorded as a localized modulation of the detector current as a function of the reference arm position. A beamsplitter 20, optical detector 22, transimpedance amplifier 24, demodulator 26, A/D converter 28, and display 30 are also shown. The detector current generated by a sample containing multiple reflecting sites distributed along its depth (such as biological tissue) contains the sum of multiple, overlapping copies of this interference pattern. A map of tissue reflectivity versus depth or "A-Scan" is obtained by scanning the reference mirror 32 at constant velocity, while recording the envelope of the detector current. The envelope may be recorded with high dynamic range by scanning the reference mirror 32 at fixed velocity, and demodulating the detector current at the resulting Doppler frequency. Cross-sectional images of tissue backscatter or "B-Scans" may be acquired by obtaining sequential A-scans while scanning the probe beam across the tissue surface using a lateral beam scanning mirror 33 or some other lateral scanning optic device. The resulting two-dimensional datasets are plotted as gray-scale or false-color images.

A significant advantage of using low-coherence interferometry for signal detection is that the interferometer 14 acts as an optical heterodyne detector, providing a dramatic expansion in dynamic range compared to direct detection of scattered light. Since the interferometric component of the detector current is proportional to the product of the electric field amplitudes returning from each arm, the detected envelope signal is proportional to the square root of the sample power reflectivity. Extremely faint reflections in the sample ($\sim 10^{-11}$ times the incident optical power) are routinely detected in A-scans recorded in a fraction of a second. As illustrated in FIG. 1, the interferometer 14 can also be implemented using inexpensive semiconductor sources and detectors, and flexible single-mode optical fibers suitable for remote imaging through minimally invasive diagnostic instruments.

Signal-To-Noise Ratio in OCDR and OCT

A significant limitation in the use of OCDR and OCT in highly scattering media is that the OCT probe light is very strongly (exponentially) attenuated in the scattering material, thus limiting the imaging depth which can be achieved in a given amount of time for a given sensitivity. For a conventional OCT system in which a 50/50 beamsplitter 20 is used in the Michelson interferometer, the signal to noise ratio (SNR) of the detected electronic signal in the shot-noise limit is given by Eq. (1) below:

$$SNR = \frac{\rho P_s R_s}{2qB} \quad (1)$$

In this expression, SNR is signal-to-noise ratio (a measure of the sensitivity which also relates to imaging depth in scattering media), $\rho$ is the detector responsivity, $P_s$ is the optical power incident on the sample, $R_s$ is the optical power reflectivity of the sample, q is the charge on the electron, and B is the detector bandwidth. The latter variable B is inversely proportional to the time required to obtain an OCDR scan or OCT image. The shot-noise limit under which this expression is calculated is well known to those practiced in the art to be the best possible performance (i.e., to give the best value for S/N) which can be achieved in an optical detection system. Even though not all implementations of OCDR and OCT may actually achieve true shot-noise limited performance and therefore may not be strictly governed by Eq. (1), most implementations aim to be near this limit and the equation is still a useful guideline illustrating the trade-offs between sensitivity, source power, and image acquisition time in this limiting case of the best possible performance.

Equation (1) makes clear that there is a trade-off between sensitivity or depth, imaging time, and the source power incident on the sample in OCDR and OCT. Increases in imaging speed, for example, may only be achieved through either a decrease in S/N or an increase in power incident on the sample. Increases in sensitivity or imaging depth (both proportional to S/N) may only be obtained by increasing either the imaging time or the power on the sample. For industrial and medical imaging applications, it is desirable to image as rapidly as possible, at a rate of at least several images per second. Recently, new technology has been developed permitting OCT image acquisition up to video rate (30 images/second), and high power low-coherence sources have become available to partially compensate for the decrease in sensitivity which necessarily accompanies any increase in imaging speed according to Eq. (1). However, these high power sources are very expensive, and still are not sufficiently powerful to allow for clinically acceptable quality imaging at video rate (or even at the ~10 images/second rate common to ultrasound imaging).

Detector Power Limitations for Shot-Noise Limited Performance

Two requirements on the amount of optical power which may be incident on the detector must be met in order to be at or near the shot-noise limit in OCDR and OCT. The first requirement is that the total optical power incident on the detector 22 cannot be arbitrarily high in order for shot noise to dominate over excess intensity noise for available sources. For systems with optical sources 16 which emit low power, this is not a problem. However, recent developments in source technology have resulted in the availability of higher power sources (10-20 mW) which are very attractive for high-speed imaging since the higher sample arm power partially compensates for the increased bandwidth B necessary for higher speed imaging, according to Eq. (1). Since most industrial and biological samples have very low reflectivity, they do not reflect an appreciable amount of sample arm light power onto the detector 22. However, in conventional systems employing such high power sources, an attenuator must be placed in the reference arm 18 in order to approach the shot noise limit. This represents a waste of up to 50% of the valuable and expensive source power, which is lost in an attenuator. It would be much better if this power could instead be directed onto the sample, so it could contribute to imaging performance as describe in Eq. (1). Clearly there is a need for an improved interferometer design for OCDR and OCT which avoids power losses due to attenuation required to achieve shot-noise-limited performance on the detector.

The second requirement on the amount of power on the detector is that it must be sufficiently high so that shot noise dominates over thermal noise in the detector. For most commonly available semiconductor detectors in the visible and near-infrared regions of the spectrum, the power on the detector must be at least approximately 1 μW for a typical low speed system using a detector with a bandwidth less than approximately 100 kHz, to 10 μW for a typical high speed system using a detector with a bandwidth of approximately 10 MHz. Thus, there is a range of acceptable power levels which will achieve shot-noise limited performance at the detector, and under the assumption that most of the light reaching the detector comes from the reference arm (i.e., under the approximation of a weakly reflecting sample), this places a limitation on the range of acceptable power levels in the reference arm, which is typically in the range of between 1 μW and 10 μW.

Reciprocal Optical Elements: The Beam splitter/Fiber Coupler

In conventional OCDR and OCT, the central element of the Michelson interferometer is a standard beamsplitter 20 which transmits or splits some fraction of the power (typically 50%) of the incident light power into each of the sample and reference arms 12 and 18. In a bulk optic interferometer the beamsplitter 20 may be a mirror with a partially reflective coating, while in a fiber optic interferometer the beamsplitter is composed of a pair of fibers partially fused together which is known as a fiber coupler. As illustrated in FIG. 2, the beamsplitter may be abstracted as a four-port optical element with two inputs (labeled as I1 and I2), and two outputs (labeled as O1 and O2). The abstracted beamsplitter illustrated in FIG. 2 is characterized by a splitting ratio α, such that a fraction α of the light power incident at port I1 (neglecting small internal losses of the beamsplitter) is transmitted to port O2, while the fraction (1−α) of the light power incident at port I1 is transmitted to port O1. A similar statement applies to light power incident at port I2: in this case, a fraction α of the light power incident at port I2 (neglecting small internal losses of the beamsplitter) is transmitted to port O1, while the fraction (1−α) of the light power incident at port I1 is transmitted to port O2. This conventional beamsplitter is known as a reciprocal optic element because light which is input into either of the output ports O1 or O2 will reciprocally be transmitted to the input ports I1 and I2. Specifically, a fraction α of any light power incident at port O1 is transmitted to port I2, while the fraction (1−α) of the light power incident at port O1 is transmitted to port I1. Finally, a fraction α of any light power incident at port O2 is transmitted to port I1, while the fraction (1−α) of the light power incident at port O2 is transmitted to port I2.

Reciprocal Power Losses in Conventional OCDR and OCT

A second clear drawback of the use of the conventional Michelson interferometer topology in OCDR and OCT is that significant reflected sample arm power is lost because it is inevitably directed back into the source, rather than being collected by the detector 22. In the theoretical analysis which leads to Eq. (1) (derived in the limit of a low reflectivity sample) the noise power is proportional to the amount of power incident on the detector 22 from the reference arm 18, while the signal power is proportional to the product of the coupler splitting ratios from the source 16 to the sample arm 12 and from the sample arm 12 to the detector 22. In the 50/50 (α=0.5) Michelson interferometer used in conventional OCT (see FIG. 1), the light from the broadband source 16 is split evenly between the sample and reference arms, while light returning from both the sample and reference arms is split again into the input arms 34 and 36 containing the source 16 and detector 22. Thus, the detected signal power is proportional to the product of the 50% splitting ratio from the source 16 to the sample arm 12, and the 50% splitting ratio from the sample arm 12 to the detector 22, for a combined sample power double splitting ratio of 25%. Fiber couplers with coupling ratios other than 50% are commonly available; however, their use in the Michelson configuration is even worse. For example, if a 90/10 beamsplitter directs 90% of the source light into the sample arm and only 10% of the light into the reference arm, then the combined sample power splitting ratio is only 9% (10% of the 90% of the source light power incident on the sample).

The modified form of Eq. (1) which is correct for the case of arbitrary splitting ratio is set forth as Eq. (2):

$$SNR = \frac{\rho P_O R_s \alpha(1-\alpha)}{qB} \quad (2)$$

Here, α is the coupler splitting ratio and $P_o$ is the source power. Eq. (2) is consistent with Eq. (1) since in the case of Eq. (1), $P_s = P_o/2$. Clearly, the SNR in Eq. (2) is optimized for α=0.5, or a 50% coupling ratio.

Motivation for the Invention

Until the development of the present invention, the only method to increase the sensitivity or acquisition rate in OCDR and OCT was to increase the source power. Increases in the source power are very expensive given current source technology. The design of conventional OCDR and OCT interferometers with reciprocal beamsplitters, is very inefficient with the expensive source power, since up to 50% of the source power is lost due to attenuation of the reference arm, and an additional 50% of the power reflected from the sample is wasted by being directed back into the source. An interferometer design which avoids both of these problems could be up to a factor approaching 4 more efficient, and could thus obtain better quality images at the high speeds required for commercial applications of OCDR and OCT technology. Thus, there is a clear need for an invention which makes more efficient use of broadband source light than the conventional OCT interferometer.

SUMMARY OF THE INVENTION

In one aspect of the invention an interferometer system includes an optical radiation source, an optical circulator connected between the optical radiation source and a sample location for transmitting optical radiation from the optical radiation source to the sample location, and an output of the optical circulator is connected to direct optical radiation to an optical detector. Various embodiments of such a system are provided.

For example, three embodiments are provided in which an interferometer includes a low coherence optical radiation source and a first beamsplitter having a first input connected to receive optical radiation from the low coherence optical radiation source. A first nonreciprocal optical element (such as an optical circulator) has a first input connected to receive optical radiation from a first output of the first beamsplitter, a first output for directing optical radiation from the first input to a sample to be imaged, a second input connected in common with the first input for receiving optical radiation reflected by the sample, and a second output for receiving optical radiation from the second input. A second beamsplitter has a first input connected to receive optical radiation from the second output of the nonreciprocal optical element, and an optical radiation detector is connected to receive optical radiation from the second beamsplitter.

Two embodiments are provided in which an interferometer include a low coherence optical radiation source and a nonreciprocal optical element (such as an optical circulator) having a first input connected to receive optical radiation from the low coherence optical radiation source and a combination first output/second input. A beamsplitter is provided with a first input connected to the combination first output/second input of the nonreciprocal optical element, a first output connected for directing optical radiation to a sample to be imaged and for receiving reflected optical radiation from the sample to be imaged, and a second output connected for directing optical radiation to a reference delay element and for receiving reflected optical radiation from the reference delay element.

Another aspect of the invention also provides a method of performing OCDR or OCT imaging of a sample which involves the steps of: (a) producing low coherence optical radiation; (b) directing at least some of the low coherence optical radiation through an optical circulator to the sample; (c) reflecting at least some of the low coherence optical radiation off of the sample; and (d) detecting at least some of the reflected low coherence optical radiation and producing an electrical signal corresponding thereto.

DETAILED DESCRIPTION

The invention, which is described in several embodiments, consists of novel interferometer designs for OCDR and OCT which employ non-reciprocal optical elements in order to make more efficient use of the source light power.

Figure 3:
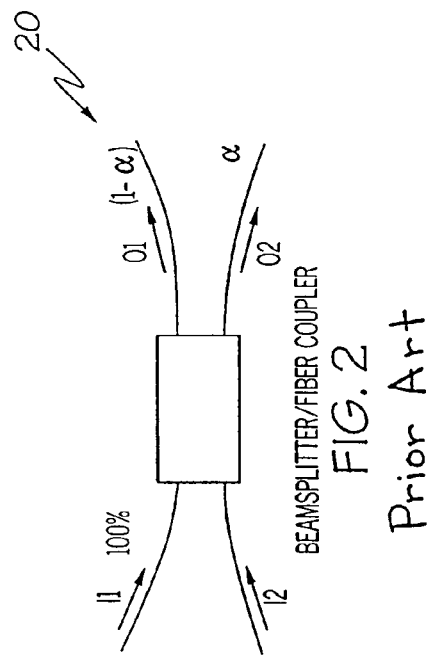
FIG. 3 is a schematic illustration of an optical circulator.

The critical technology which enables the present invention are nonreciprocal optical elements which have recently become commercially available, such as the optical circulator (OC) and Faraday Rotator (FR). An optical circulator 50, as illustrated in FIG. 3, is a threeport optical device in which all power incident on input port I1 (except for small internal losses) is directed into output port O1, which is common with the second input port I2. All light incident on the input port I2 (except for small internal losses) is similarly directed into the output port O2. Polarization-independent optical circulators are commercially available, in which the performance is independent of the polarization state of the light at the input or output ports. Bulk-optic and fiber-optic versions are commercially available; fiber-optic versions are particularly suitable for use in fiber-optic implementations of OCDR and OCT. An example of a commercially available fiberoptic optical circulator which would be suitable for use in the designs disclosed in this application is Model #60-13-3 from Princeton Optics, Inc., of Ewing, N.J.

Figure 4:
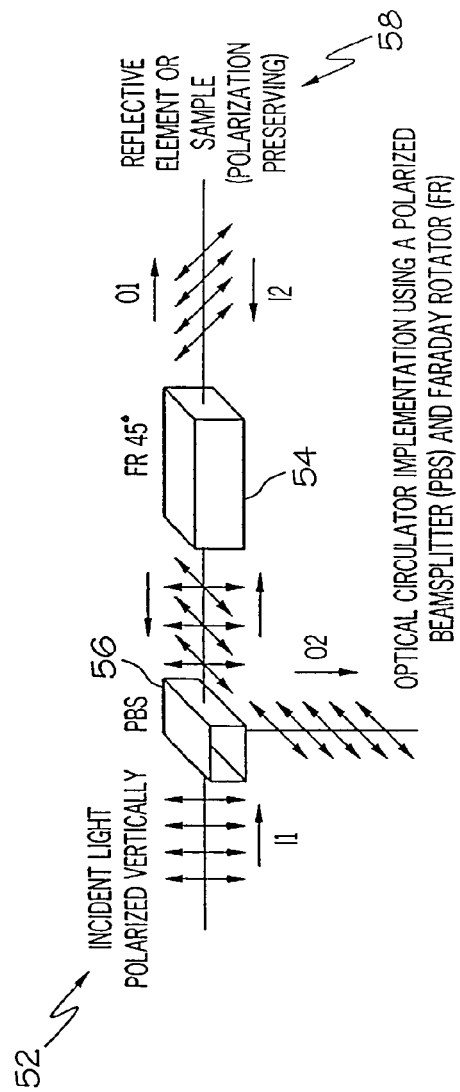
FIG. 4 is a schematic illustration of an optical circulator implemented using a polarizing beamsplitter and a Faraday rotator.

A second nonreciprocal optical element suitable for use in improving the performance of OCDR and OCT is the Faraday rotator. A Faraday rotator is a device which rotates the polarization state of a light beam which traverses it, by an angle which is a characteristic (fixed or variable) property of the rotator. In particular, a polarization-dependent form of optical circulator 52 may be constructed from a 45° Faraday rotator 54 and a polarizing beamsplitter (PBS) 56, as illustrated in FIG. 4. A polarizing beamsplitter 56 is an optical device which either transmits or reflects light incident upon it depending upon the polarization state of the incident-light. As illustrated in FIG. 4, vertically polarized light incident on a PBS 56 oriented as illustrated will pass through the PBS 56 and be incident on the FR 54. The rotation state of the light will be rotated by 45° by the FR 54, and may then be directed onto a reflective element or sample 58, which must preserve the polarization state of the light reflected. The reflected light will be rotated another 45° by the FR 54, and will then be reflected by the PBS 56 since its polarization state has been rotated by a total of 90° from that of the incident light. This configuration is effectively a form of optical circulator 52, in which the incident light is considered as entering port I1, the transmitted and reflected light transit ports O1 and I2, respectively, and the output light exits port O2. It should be noted that the device illustrated in FIG. 4 is just one possible implementation of an optical circulator, and this is not an optimal implementation in many cases because the polarization state of the light entering port I2 must match the polarization state of the light exiting port O1, thus the sample must preserve polarization. Optical circulators are commercially available which allow for arbitrary polarization states at any of the input ports I1 or I2. Thus, in the remainder of this technical description reference will be made only to optical circulators in general, and not specifically the PBS/FR implementation. However, it should be understood that this implementation may be used whenever the sample does in fact preserve the polarization state of the light reflected from it, and this implementation may in fact be less expensive than the alternative in that case. An example of a polarizing beamsplitter and a Faraday rotator suitable for use in the designs disclosed in this application are Model #10FC16 from Newport Corporation, Irvine, Calif., and Model #MOFI6CW100000 from E-Tek Dynamics, San Jose, Calif., respectively.

Figure 5:
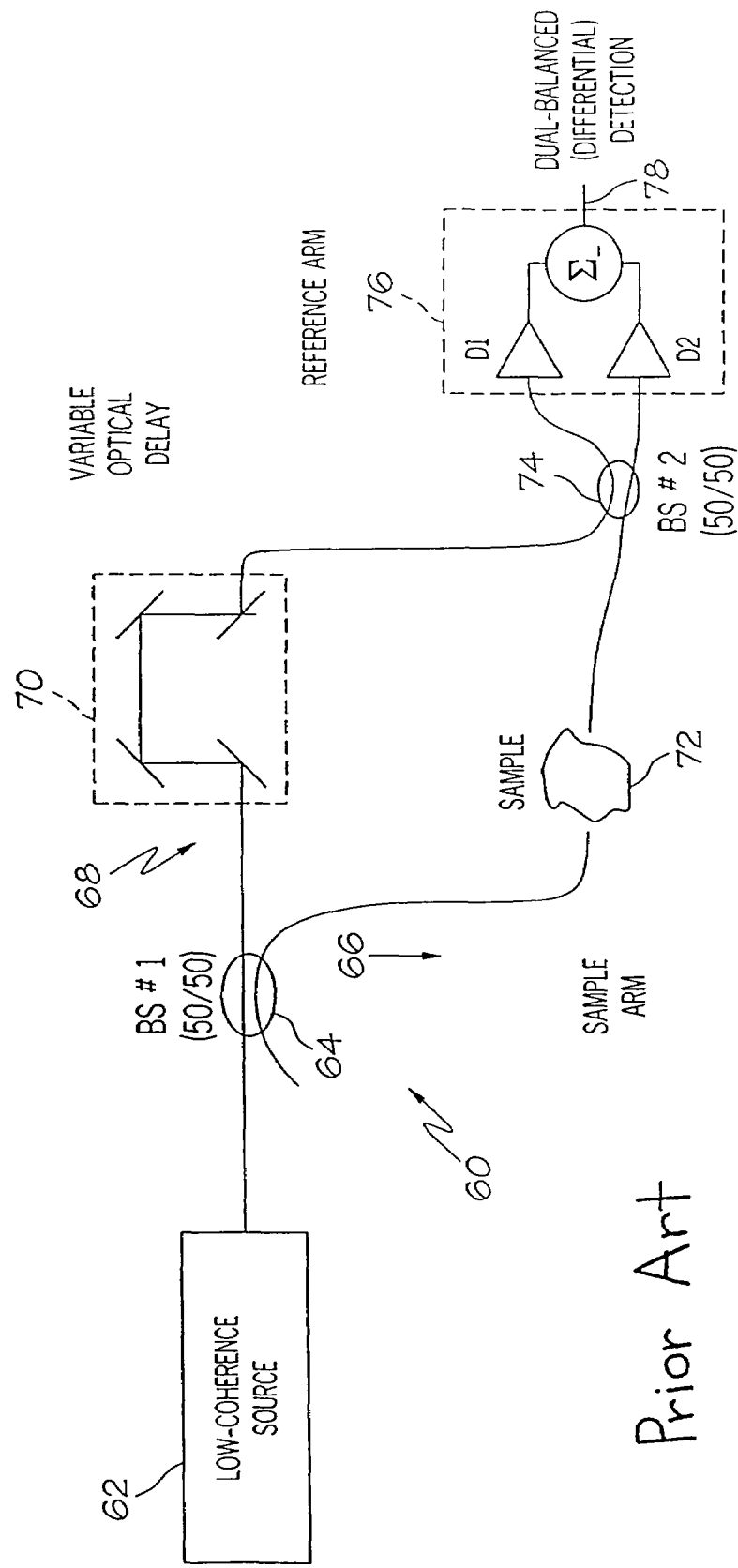
FIG. 5 is a schematic illustration of a Mach-Zehnder interferometer configuration.

A second enabling technology for the improved efficiency OCDR/OCT designs disclosed in this application is the use of dual-balanced (differential) detection of optically heterodyned signals. Dual-balanced detection is useful when two optical signals with approximately equal DC power, but with AC components which are 180° out of phase, are both present. This is the case, for example, in previously published transmissive implementations of OCDR and OCT which employ a Mach-Zehnder interferometer configuration 60 as illustrated in FIG. 5. The low-coherence source light 62 is incident on the first beamsplitter 64, which splits the light evenly between sample 66 and reference 68 arms. The reference arm 68 includes a variable optical delay 70, while the sample arm 66 includes an optical element or sample 72, which is illuminated in transmission. Light from the sample and reference arms is recombined in the second beamsplitter 74, and the resulting mixed light is split evenly between two detectors D1 and D2 whose responsivity is carefully matched. These detectors D1 and D2 are placed in an electronic circuit 76 whose output 78 is equal to the amplified difference between the photocurrents produced by the two detectors. This detection scheme has two advantages. First, since the light intensity incident on each detector surface as a function of reference arm delay is 180° out of phase, the envelope of difference signal between the two detector currents (as the reference delay is scanned) is equal to twice the amplitude of the AC component of the photocurrent of each detector. Secondly, since any excess noise present in the light propagating through the interferometer will be common to both detectors, this excess noise will be eliminated by the difference operation. This detection scheme depends upon careful matching of the DC component of the light power incident on each detector as well as the careful matching of the responsivities of both detectors to be effective, although self-balancing detectors which include self-adjusting variable gains for the two detectors are commercially available. An example of a high sensitivity auto-balancing photodetector suitable for use at low frequencies in the designs disclosed in this application is Model #2007 from New Focus Corporation, of Santa Clara, Calif., and a balanced receiver suitable for high-frequency applications is Model #1607, from the same vendor.

The final technology which is different from most previous implementations for OCDR and OCT which is desirable for the novel high-efficiency embodiments is single-mode fiber optic couplers or beamsplitters with splitting ratios other than 50/50. In this application, we will denote such "unbalanced" couplers as having a splitting ratio of $\alpha$, indicating that the fraction $\alpha$ of the light power incident on port I1 is transmitted to port O2, while the fraction $(1-\alpha)$ of the light power incident on port I1 is transmitted to port O1, and so on. Using this notation, the standard 50/50 beamsplitter has $\alpha=0.5$. Such unbalanced beamsplitters are very commonly commercially available in the fiber optic marketplace. An example of a singlemode fiber coupler with a splitting ratio of 90/10 which is suitable for use in the designs disclosed in this application is Model #28 CBB 102/001/AS from Melles Griot Corporation, Irvine, Calif. Other couplers with arbitrary splitting ratios are available from this and other vendors.

Novel OCDR/OCT Interferometer Designs

We disclose five novel interferometer configurations which simultaneously avoid the losses associated with reference arm attenuation and with reciprocal power losses in conventional OCDR/OCT. These configurations are illustrated in FIGS. 6-10. Most of these configurations involve unbalanced splitters. In this disclosure, we first describe the design qualitatively. Then, for each embodiment, design equations are provided for optimizing the splitting ratios in order to obtain maximum signal to noise for a given source power and minimum power required by the detector for shot noise-limited performance. Finally, for each embodiment, typical values are presented assuming typical values in the design equations. In each interferometer configuration the various optical elements could typically be interconnected using fiber optic technology, but it is recognized that other technologies such as integrated-optic or conventional bulk-optic (i.e. discrete optical elements) could also be used for interconnection of the optical elements.

Embodiment #1

Figure 6:
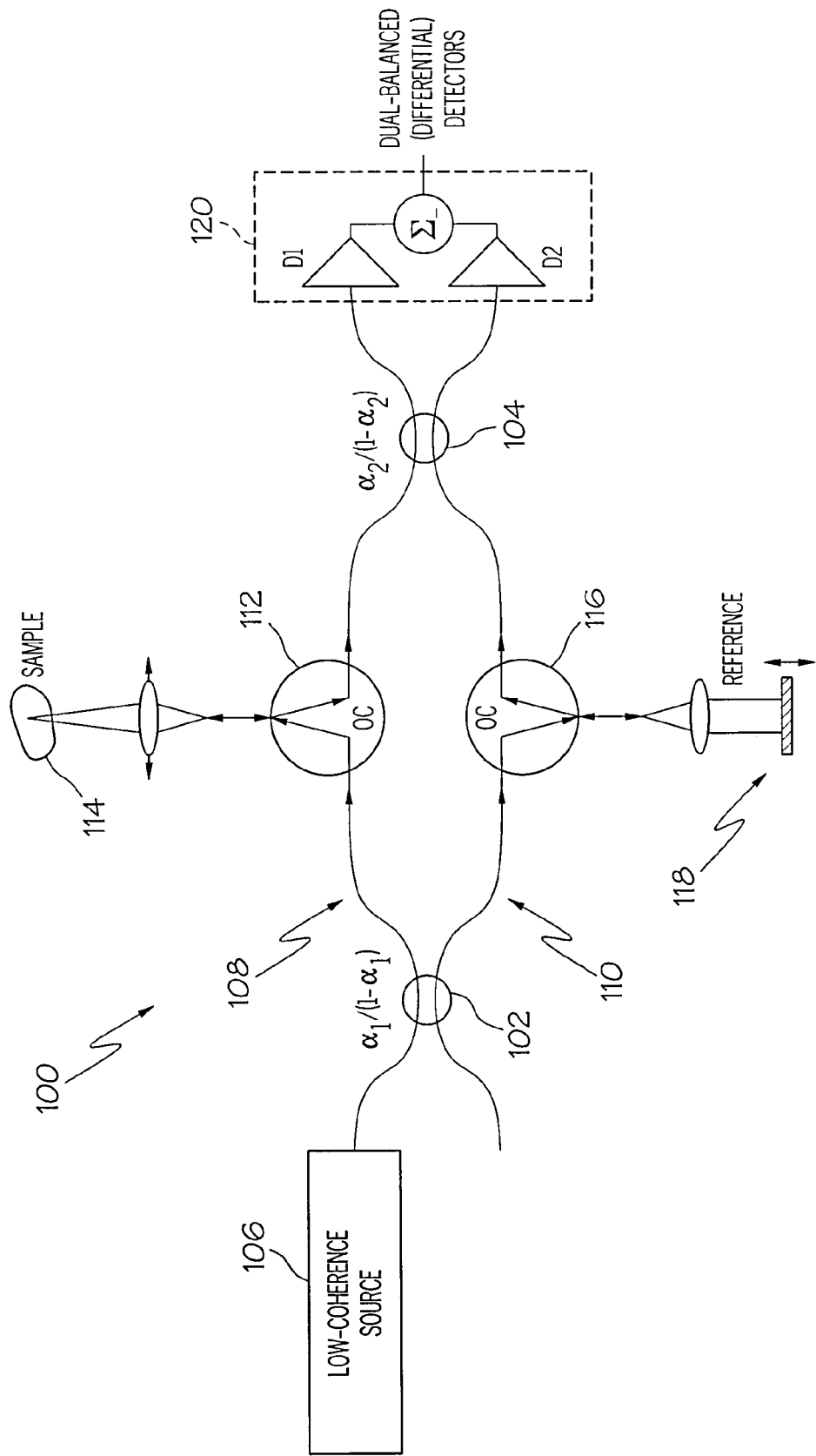
FIG. 6 is a schematic illustration of one interferometer embodiment according to the invention.

The embodiment illustrated in FIG. 6 uses an interferometer configuration 100 similar to the Mach-Zehnder illustrated in FIG. 5, except that both couplers or beamsplitters 102 and 104 may be unbalanced. In FIG. 6, an unbalanced singlemode coupler 102 splits light from the source 106 and sends most of the source light power to the sample arm 108 of the interferometer 100. The splitting ratio of the unbalanced coupler 102 is selected such that the amount of power directed into the reference arm 110 is within the suitable range for shot-noise limited detection. An optical circulator 112 directs the sample arm light onto the sample 114, and directs light returning from the sample into a second singlemode coupler 104, which in general may also be unbalanced. In the reference arm 110, a second optical circulator 116 directs reference arm light onto a variable reference delay element 118, and directs light returning from the delay 118 into the other input port of second single mode coupler 104. This configuration places most of the source light on the sample 114, thus automatically eliminating the power loss in the conventional interferometer due to purposeful attenuation of reference arm light to achieve shot-noise limited detection. Secondly, this configuration directs all of the light returning from the sample 114 to a detector 120, thus none of the reflected sample arm light is lost to reciprocal losses as in the conventional design. The intensities incident on the detectors D1 and D2 as a function of reference arm delay are out of phase, so differential detection may be achieved simultaneous with common-mode rejection of excess intensity noise.

If the splitting ratio of the second splitter 104 is chosen to be 50/50 (i.e., $\alpha_2=0.5$), then equal powers are incident on each of the dual detectors D1 and D2, and true dual-balanced detection may be achieved. In this case, the expression for the signal-to-noise ratio is given as Eq. (3):

$$SNR = \frac{\rho P_0 (1-\alpha_1) T_c^2 R_s}{qB} \qquad (3)$$

where $\rho$ is the detector responsivity, $P_0$ is the optical source power, $\alpha_1$ is the splitting ratio of the first singlemode coupler 102, $T_c$ is the transmission through the circulator, $R_s$ is the reflectivity of the sample, q is the electronic charge, and B is the bandwidth of the detection electronics. We also disclose an expression for the optimal splitting ratio for the first coupler 102, which ensures that there is sufficient reference arm power to allow for shot-noise limited detection, but at the same time places the maximum possible power on the sample. This expression is given as Eq. (4):

$$\alpha_1 = \frac{2 P_{min}}{P_0 T_c^2 R_r} \qquad (4)$$

where $R_r$ is the reflectivity of the reference arm delay line. Here, $P_{min}$ is the minimum power which must be present at the detector 120 in order to ensure shot noise dominates receiver noise. Assuming the typical value of $P_{min}=10$ μW, the values of $P_0=10$ mW, $T_c=0.85$, and $R_r=0.9$, we obtain an optimal splitting ratio for the first coupler of $\alpha_1=0.0031$. Using a coupler with this splitting ratio as the first coupler 102 in FIG. 6, and a coupler with the value of $\alpha_2=0.5$ as the second coupler 104 provides a signal-to-noise ratio advantage of a factor of 2.88 (or 4.60 dB) over the conventional Michelson OCDR/OCT arrangement. Thus, using this optimal embodiment, OCT images could be obtained at the same rate with a factor of 2.88 times better sensitivity, or alternatively at an acquisition rate of 2.88 times faster with the same sensitivity as in conventional OCT. The use of embodiment #1 with $\alpha_2=0.5$ allows for the maximum possible gain in dynamic range as compared to the conventional design, and will be the preferred embodiment of all of those disclosed when absolutely the highest dynamic range performance must be achieved regardless of the added expense of two optical circulators 112 and 116.

The splitting ratio of the second splitter 104 in embodiment #1 may in general be chosen to be any value, however a convenient choice may be to choose a high splitting ratio, for example $\alpha_2=\alpha_1$, and then to use only the top detector D1 for signal detection. This alternative form of embodiment #1 eliminates the expense of the second matched detector D2 and the associated differential gain electronics. In this case, the expression for the signal-to-noise ratio is given as Eq. (5):

$$SNR = \frac{\rho P_0 (1-\alpha_1)(1-\alpha_2) T_c^2 R_s}{qB} \qquad (5)$$

where $\alpha_1 = \alpha_2$ is the splitting ratio of both couplers 102 and 104, and $P_i$ is the source power. In this case of $\alpha_2 = \alpha_1$ the expression for the optimal value of $\alpha_1$ is given as Eq. (6):

$$\alpha_1 = \alpha_2 = \sqrt{\frac{P_{\min}}{P_0 T_c^2 R_r}} \qquad (6)$$

Under the same assumptions that $P_{min} = 10$ μW, $P_0 = 10$ mW, $T_c = 0.85$, and $R_r = 0.9$ as stated above, the optimal value of both couplers is then $\alpha_2 = \alpha_1 = 0.039$, and the corresponding signal to noise ratio advantage over conventional OCDR/OCT is a factor of 2.67 (or 4.26 dB).

Embodiment #2

Figure 7:
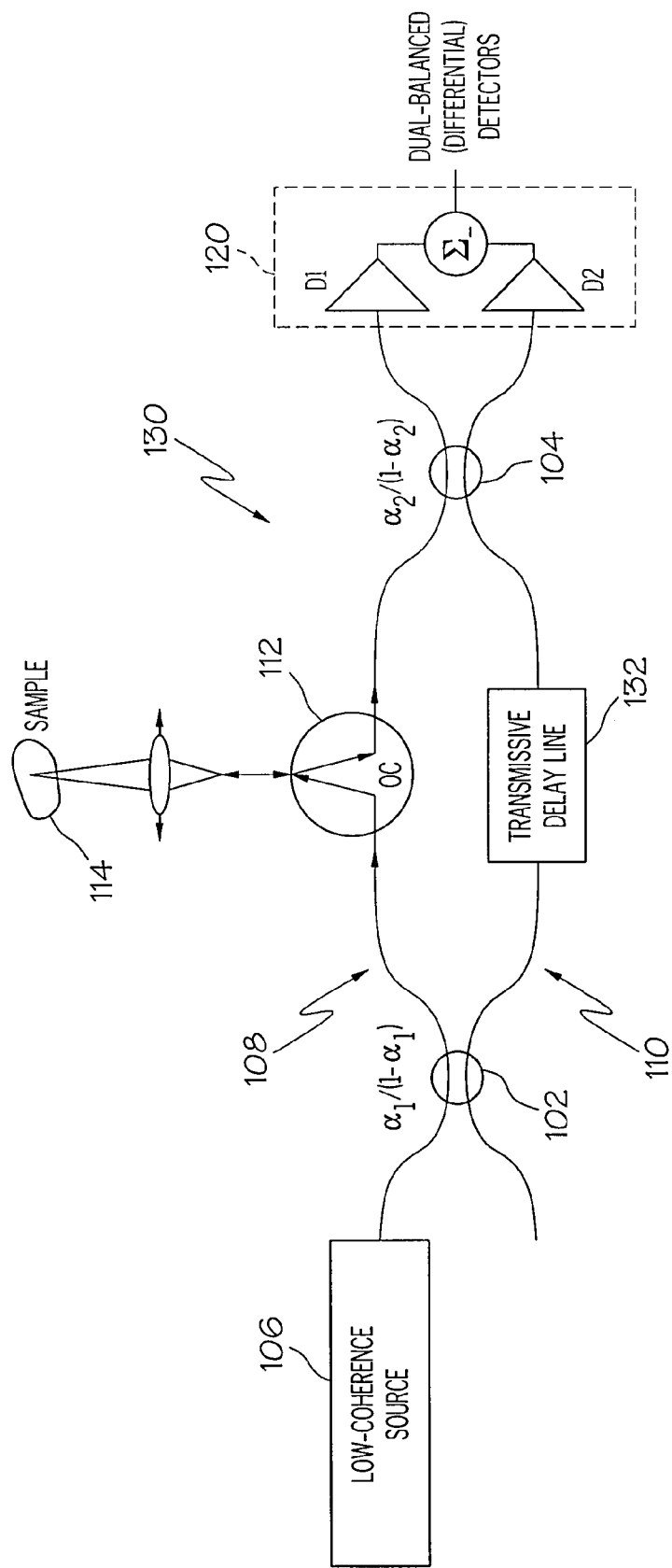
FIG. 7 is a schematic illustration of another interferometer embodiment according to the invention.

The interferometer 130 illustrated in FIG. 7 is similar to that illustrated in FIG. 6, except that the expense of one of the optical circulators is avoided by use of a transmissive delay element 132 rather than a reflective reference arm delay. The transmissive delay element 132 could be similar to element 70 illustrated in FIG. 5. All other advantages of the first embodiment are preserved. The expression for the signal-to-noise ratio in the case of $\alpha_2 = 0.5$ (dual-balanced detection) is the same as equation (3), in which case the expression for the optimal first coupler splitting ratio is:

$$\alpha_1 = \frac{2 P_{\min}}{P_0 R_r} \qquad (7)$$

Under the assumptions that $P_{min} = 10$ μW, $P_0 = 10$ mW, $T_c = 0.85$, and $R_r = 0.9$, the optimal value of the first coupler is then $\alpha_1 = 0.0022$, and the corresponding signal-to-noise ratio advantage over conventional OCDR/OCT is a factor of 2.88 (or 4.59 dB), which is identical to the dual-detector version of embodiment #1. The expression for the signal-to-noise ratio in the case of $\alpha_2 = \alpha_1$ (one detector only) is the same as equation (5); in this case the expression for the optimal coupler splitting ratio is:

$$\alpha_1 = \alpha_2 = \sqrt{\frac{P_{\min}}{P_0 R_r}} \qquad (8)$$

In equations (7) and (8), the term $R_r$ represents reference delay line transmission, rather than reflectivity, since a transmissive delay line is used rather than a reflective one. Under the assumptions that $P_{min} = 10$ μW, $P_0 = 10$ mW, $T_c = 0.85$, and $R_r = 0.9$, the optimal value of both couplers is then $\alpha_2 = \alpha_1 = 0.033$, and the corresponding signal-to-noise ratio advantage over conventional OCDR/OCT is a factor of 2.70 (or 4.31 dB), which is nearly identical to the single-detector version of embodiment #1. The performance advantages for both versions of this embodiment over conventional OCDR/OCT are the same as for interferometer 100. Interferometer 130 will be the preferred embodiment when implementation of a transmissive delay line is practical, such as in recently published high-speed OCT systems which use a novel reference delay based on Fourier transform pulse shaping techniques, which are readily amenable to implementation in a transmissive geometry.

Embodiment #3

Figure 8:
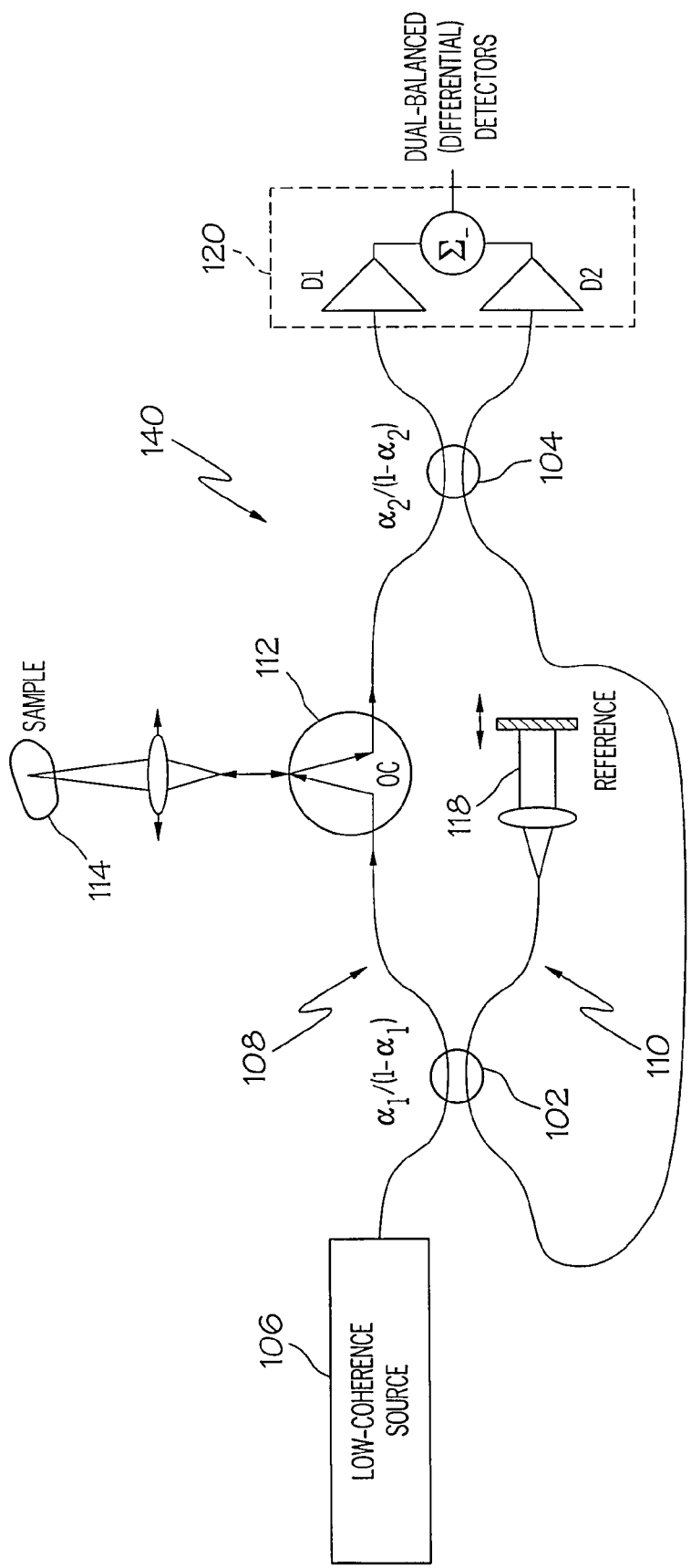
FIG. 8 is a schematic illustration of another interferometer embodiment according to the invention.

The interferometer 140 illustrated in FIG. 8 is also similar to the first embodiment of FIG. 6, except that interferometer 140 avoids the additional expense of one optical circulator while still using a reflective reference delay 118. This embodiment preserves all of the advantages of the first embodiment, except that the gain in dynamic range as compared to the conventional system is slightly less, because the optimal value of the first coupler 102 splitting ratio is somewhat smaller than in embodiment #1 in order to compensate for the small amount of reference arm power which is returned to the source 106 rather than placed on a detector. Interferometer 140 will be the preferred one when a slight loss in efficiency is worth the savings of the cost of one optical circulator.

If the splitting ratio of the second beamsplitter 104 in interferometer 140 is chosen to be 50/50 (i.e., $\alpha_2 = 0.5$), then equal powers are incident on each of the dual detectors D1 and D2, and true dual-balanced detection may be achieved. In this case, the expression for the signal-to-noise ratio is the same as Eq. (3). The expression for the optimal splitting ratio for the first coupler 102, which ensures that there is sufficient reference arm power to allow for shot-noise limited detection, but at the same time places the maximum power on the sample 114, under the assumption that $\alpha_1$ is small, is the same as given in equation (7). Thus, the typical value of rhte optimum splitting ratio $\alpha_1$ and the performance advantage of this embodiment over the conventional Michelson arrangement (under the assumption that $\alpha_1$ is small) are exactly the same s for the dual-detector version of embodiment #2. The use of interferometer 140 with $\alpha_2 = 0.5$ allows for the second-highest possible gain of all reflective delay embodiments disclosed in dynamic range as compared to the conventional design, and will be the preferred embodiment when a reflective delay element must be used and the expense of a second optical circulator as required in interferometer 100 of FIG. 6 must be avoided.

The splitting ratio of the second splitter 104 in interferometer 140 may in general be chosen to be any value, however a convenient choice may be to choose a high splitting ratio, for example $\alpha_2 = \alpha_1$ and then to use only the top detector D1 for signal detection. This alternative form of interferometer 140 eliminates the expense of the second matched detector D2 and the associated differential gain electronics. In this case, the expression for the signal-to-noise ratio is the same as Eq. (5). In this case of $\alpha_2 = \alpha_1$, under the assumption that both $\alpha_1$ and $\alpha_2$ are small, the optimal values for $\alpha_2$ and $\alpha_1$ are the same as given in equation (8). Thus, the typical value for the optimum splitting ratios $\alpha_2$ and $\alpha_1$ and the performance advantage of this embodiment over the conventional Michelson arrangement (under the assumption that both $\alpha_2$ and $\alpha_1$ are small) are exactly the same as the single-detector version of embodiment #2.

Embodiment #4

Figure 9:
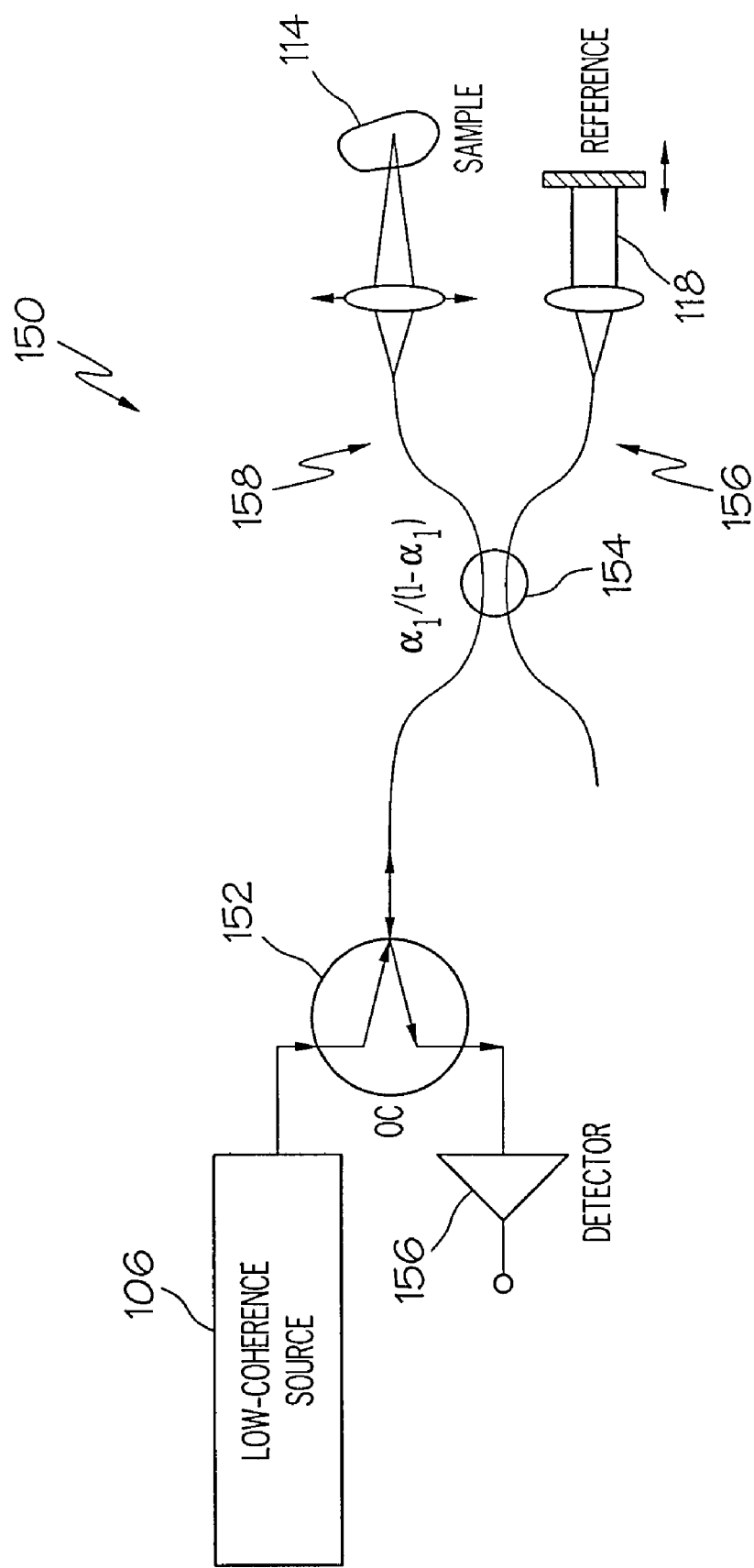
FIG. 9 is a schematic illustration of another interferometer embodiment according to the invention.

The interferometer 150 illustrated in FIG. 9 is similar to the conventional Michelson interferometer arrangement, except that an optical circulator 152 is placed between the low-coherence source 106 and the fiber coupler or beamsplitter 154 and the beamsplitter 154 is unbalanced. The splitting ratio of the unbalanced coupler 154 is selected such that the amount of power directed into the reference arm 156 is small enough to allow for shot-noise limited detection, but large enough to avoid thermal detector noise. The optical circulator 152 directs most of the light reflected from the sample 114 but only a small fraction of the light returning from the reflective reference delay element 118 onto the detector 156. Only a single detector 156 is needed in this configuration. This interferometer configuration places most of the source light on the sample 114, thus automatically eliminating the power loss in the conventional interferometer due to purposeful attenuation of reference arm light to achieve shot-noise limited detection. Secondly, most of the light returning from the sample is directed to the detector 156, thus only a small fraction of the reflected sample arm light is lost to reciprocal losses as in the conventional design.

The expressions and typical values for the signal-to-noise ratio and for the optimal coupler splitting ratios for interferometer 150 are given above as Eqs. (5) and (6), respectively. The performance advantages for this embodiment over conventional OCDR/OCT are the same as for the second implementation (with $\alpha_2=\alpha_1$,) of embodiment #1 of FIG. 6, i.e. a signal-to-noise advantage of 2.67 (4.26 dB) as compared to conventional OCDR/OCT. Interferometer 150 is a preferred embodiment to the $\alpha_2=\alpha_1$, versions of embodiments #1 and #2, since it achieves the same performance with fewer components, i.e. with only one unbalanced coupler and one optical circulator.

Embodiment #5

Figure 10:
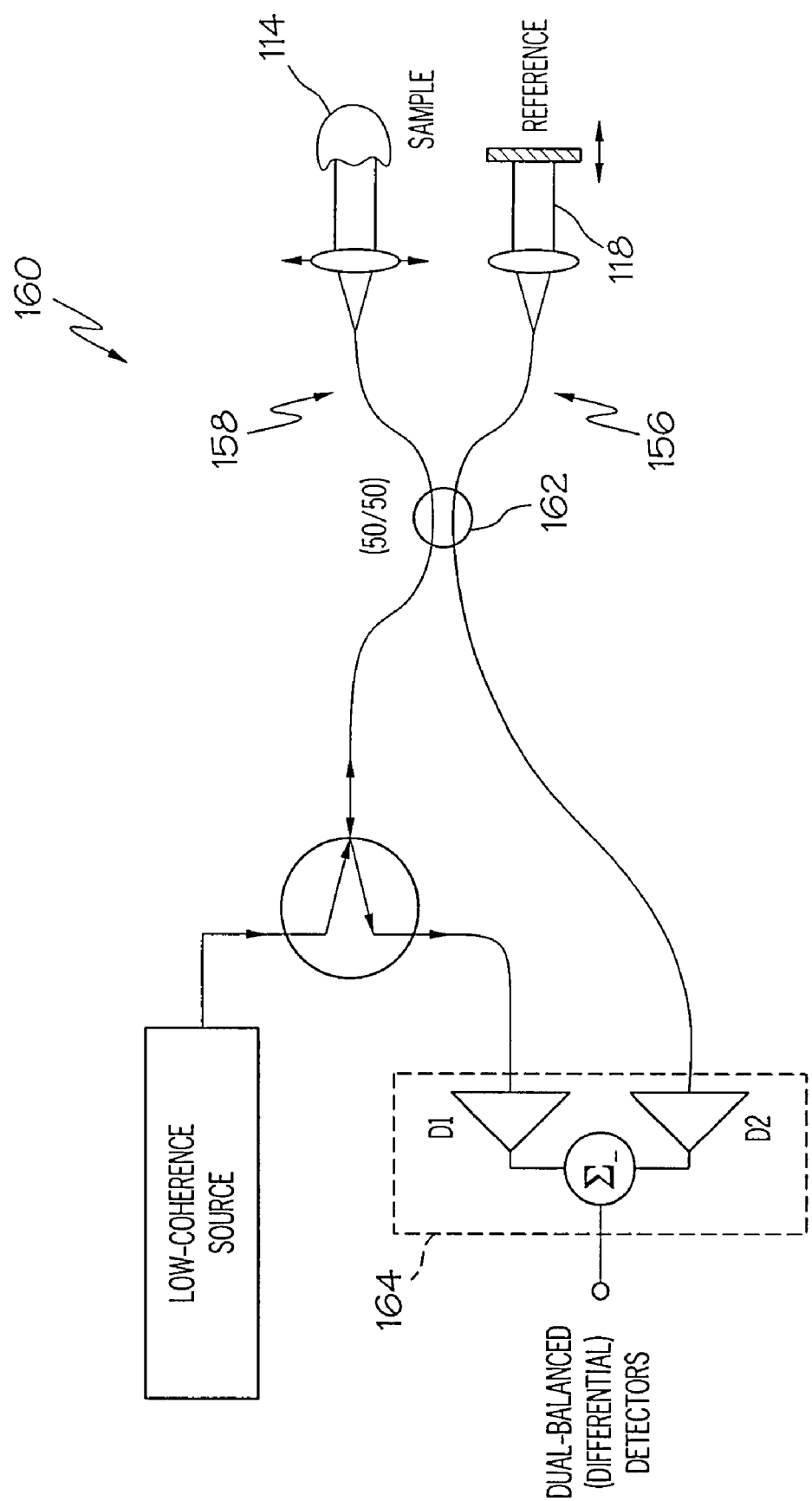
FIG. 10 is a schematic illustration of another interferometer embodiment according to the invention.

The interferometer 160 illustrated in FIG. 10 is similar to that illustrated in FIG. 9, except that a balanced coupler 162 is used in place of the unbalanced coupler 154 in FIG. 9, and a dual-balanced detector arrangement 164 is also used. This interferometer configuration does riot have the advantage of placing most of the source light on the sample, thus it will not be the preferred embodiment when the source power is sufficient to preclude shot-noise limited detection. However, this interferometer configuration avoids both sample and reference arm reciprocal losses by placing all of the light reflected from the sample and reference arms 158 and 156 on a detector 164, and achieves a gain in dynamic range of a factor of approximately 1.45 (1.60 dB) as compared to the conventional arrangement. This will be the preferred embodiment when a low-power source is used and the expense of an unbalanced coupler must be avoided.

General Expression for Optimization of Coupler Splitting Ratios

We disclose a general procedure for optimizing the choice of coupler splitting ratios for those embodiments employing two beamsplitting couplers. This procedure seeks to balance the requirements to place the largest possible fraction of the source power on the sample, while at the same time ensuring that there is sufficient power in the reference arm to ensure shot-noise limited detection for weakly reflective samples. For embodiments #1 and #2, this expression is given by equation (9):

$$\alpha_1 \alpha_2 = \frac{P_{\min}}{P_0 T_c^2 R_r}. \tag{9}$$

For embodiment #2, there is no reference arum circulator, so expression (9) applies if $T_c$, is taken to be 1, and $R_r$ is taken to mean reference delay line transmission, rather than reflectivity. According to Eq. (9) there are an infinite number of possible choices for $\alpha_1$, and $\alpha_2$, however the choices $\alpha_2=0.5$ (i.e., a 50/50 splitting ratio for the second coupler) and $\alpha_1=\alpha_2$ (i.e., the same splitting ratio for both couplers) are particularly useful. For embodiment #3, the expression which optimizes the choice of splitting ratios is given by Eq. (10):

$$\alpha_1(1-\alpha_1)\alpha_2 = \frac{P_{\min}}{P_0 R_r} \tag{10}$$

As seen from the above embodiments, the primary commonality between the interferometer configurations is the use of at least one nonreciprocal optical element (preferably an optical circulator) which results in increased efficiency. However, although generally undesirable it is recognized that interferometer configurations in accordance with the present invention could be constructed with a relatively low efficiency (an efficiency similar to that of traditional systems).

Each of the various embodiments described provides an interferometer system including an optical radiation source, a first optical circulator and an optical detector. A first optical path extends from the optical radiation source, through a first portion of the first optical circulator to a sample location, and from the sample location through a second portion of the optical circulator to the optical detector.

In the embodiments of FIGS. 6-8, the interferometer system also includes a first beamsplitter positioned between the optical radiation source and the optical circulator along the first optical path, and a second beamsplitter positioned between the optical circulator and the optical detector along the first optical path. In the embodiment of FIG. 9, the interferometer system includes a second optical path extending from the optical radiation source, through the first portion of the optical circulator to a reference location, from the reference location through the second portion of the optical circulator to the optical detector. In the embodiment of FIG. 10 the optical detector comprises first and second optical detectors, the first optical detector positioned at the end of the first optical path, and the interferometer further includes a second optical path extending from the optical radiation source, through the first portion of the optical circulator to a reference location, from the reference location to the second optical detector.

The forgoing optimization equations were derived assuming shot noise limited detection. This analysis is not adequate in situations where there is appreciable backreflection from the sample arm optics or when the optical source intensity noise exceeds the excess photon noise predicted by the photon arrival statistics given the source bandwidth. In these cases, the following SNR analysis, which is more complete, should be used to optimize the splitting ratio. Note that some notation used hereafter differs from that used in the previous analysis.

In a dispersionless OCT system, the photocurrent at a detector will in general be given by $I_d = \rho(P_r + P_s + P_x + 2\sqrt{P_r P_s}\cos(k_0 \Delta l))$, where $\rho$ is the detector responsivity. $P_r$ is the optical power incident on the photodetector reflected from the reference arm of the interferometer, $P_s$ is that portion of the optical power incident on the photodetector having been backscattered from the sample that is coherent with the reference light, and $P_x$ is the optical power incident on the photodetector reflected from the sample arm of the interferometer which is incoherent with the reference light. Also, $k_0$ is the center wavenumber of the optical source, and $\Delta l$ is the optical path difference between the reference and sample arms. The signal photocurrent, $I_s$, is the a.c., or interference term of $I_d$:

$$I_s = 2\rho\sqrt{P_r P_s}\cos(k_0 \Delta l) \quad (11)$$

We express noise sources in terms of the photocurrent variance $\sigma_i^2$. The noise sources to be included in this analysis are receiver noise $\sigma_{re}^2$, shot noise $\sigma_{sh}^2$, and excess intensity noise $\sigma_{ex}^2$. Receiver noise may be modeled as thermal noise in a resistance-limited receiver with an effective load resistance $R_{eff}$. Thermal noise is the random thermal motion of electrons in a conductor, and the photocurrent variance due to thermal noise is given by: $\sigma_{re}^2 = 4k_B TB/R_{eff}$, where $k_B$ is Boltzman's constant, T is temperature and B is the detection bandwidth. For a commercial photoreceiver module, the photocurrent variance due to receiver noise can be calculated directly from the manufacturer specifications. For example, the manufacturer may specify input noise current (noise equivalent photocurrent density, e.g. 2 pA/√Hz), from which we calculate: $\sigma_{re}^2 = (2\ \rho A/\sqrt{Hz})^2 B$. The random arrival of photons from a monochromatic light source is a Poisson process. The resulting photocurrent variance is shot noise and is given by $\sigma_{sh}^2 = 2qI_{dc}B$, where q is the electronic charge and $I_{dc}$ is the mean detector photocurrent. The random arrival of photons from a broadband, incoherent light source is a Bose-Einstein process. The resulting photocurrent variance has two terms: shot noise, and excess photon noise. Excess photon noise is given by $\sigma_{exp}^2 = (1+V^2)I_{dc}^2 B/\Delta\nu$, where V is the degree of polarization of the source, and $\Delta\nu$ is the effective linewidth of the source. Assuming a Gaussian power spectral density, $\Delta\nu = \sqrt{\pi/2\ln(2)} c\Delta\lambda_{FWHM}/\lambda_0^2$, where c is the speed of light, $\Delta\lambda_{FWHM}$ is the full-width half-maximum wavelength bandwidth of the source, and $\lambda_0$ is the center wavelength. This expression for excess photon noise represents the minimum expected intensity noise for a source with a given effective linewidth. Some broadband optical sources, such as mode-locked femtosecond lasers, exhibit more than this minimum intensity noise. In order to generalize, we will write another expression for excess intensity noise (or relative intensity noise): $\sigma_{ex}^2 = (RIN)I_{dc}^2 B$. Here, RIN (relative intensity noise) may be specified by the manufacturer of the source, or it may be measured, or it may be calculated as $RIN = (1+V^2)\Delta\nu$, which should be valid for the broadband, incoherent sources typically used in OCT and OCDR. If RIN is calculated using the expression above, then $\sigma_{ex}^2$ is identical to $\sigma_{exp}^2$.

Assuming that the light intensity backscattered from the sample is negligible compared to the reference power, the average, or d.c. photocurrent is given by $I_{dc} \equiv \langle I_d \rangle = \rho(P_r + P_x)$, where the brackets indicate the mean value. Thus, for the case of a single detector, the total photocurrent variance is given by:

$$\sigma_i^2 = \sigma_{re}^2 + \sigma_{sh}^2 + \sigma_{ex}^2. \quad (12)$$

If balanced heterodyne detection is used, then excess intensity noise is largely cancelled. Taking into account extra retroreflected power from the sample arm, $P_x$, however, a component of the excess photon noise remains which is called beat noise and is given by $\sigma_{be}^2 = 2(1+V^2)I_r I_x B/\Delta\nu$, where $I_r = \rho P_r$ and $I_x = \rho P_x$. Noise in each of the detectors comprising the balanced receiver is independent, so their variances add and the total photocurrent variance in the case of balanced heterodyne detection becomes:

$$\sigma_i^2 = 2(\sigma_{re}^2 + \sigma_{sh}^2 + \sigma_{be}^2). \quad (13)$$

It is important to note that all photocurrent variances have been written in terms of one-sided noise spectral density functions (i.e. integrated over positive frequencies only), and that however demodulation is performed, B is the width of the detection band-pass filter, as opposed to, for example, the cutoff frequency of a demodulation low-pass filter.

Other noise sources that are generated in an OCT system include flicker (1/f) noise, dark current noise, and quantization noise. Flicker noise is avoided simply by ensuring a high enough signal carrier (heterodyne) frequency such that the signal bandwidth is well above dc (several kHz is sufficient). Dark current noise is the shot noise arising from the detector dark current. It is generally small, and because it is independent of incident light intensity, it is suppressed by the identical method as suppressing receiver noise, that is, allowing sufficient light on the detector such that shot noise dominates. Quantization noise arises from an insufficient number of A/D bits sampling the signal. This can be avoided by selecting an A/D converter with a sufficient dynamic range (the noise floor should be less than ½ of the least significant bit), and by conditioning the signal such that it fills the A/D dynamic range. Because these noise sources can be suppressed or avoided, they are not included in this SNR model.

We define $SNR = \langle I_s^2 \rangle / \sigma_i^2$. From equation (11) above, the mean-square signal photocurrent in a single detector can be written as:

$$\langle I_s^2 \rangle = 2\rho^2 P_r P_s. \quad (14)$$

For a balanced receiver, the total signal photocurrent is the sum of the photocurrent in each detector, so the mean-square signal photocurrent becomes:

$$\langle I_s^2 \rangle > 8\rho P_r P_s. \quad (15)$$

From the definition of SNR and from equations (12) and (14), SNR for a single-detector interferometer can be written in terms of $P_r$, $P_s$, and $P_x$, which can be specified for a given interferometer configuration:

$$SNR_{sd} = \frac{2\rho^2 P_r P_s}{\sigma_{re}^2 + 2q\rho(P_r + P_x)B + (RIN)\rho^2(P_r + P_x)^2 B}. \quad (16)$$

Similarly, from equations (13) and (15), the expression for SNR for a balanced-receiver interferometer configuration can be written:

$$SNR_{bd} = \frac{4\rho^2 P_r P_s}{\sigma_{re}^2 + 2q\rho(P_r + P_x)B + 2(1+V^2)\rho^2 P_r P_x B/\Delta\nu}. \quad (17)$$

For each interferometer configuration to be discussed, expressions for $P_r$, $P_s$, and $P_x$ will be specified, and $\sigma_{re}^2$ (which is independent of source power or interferometer topology) should be calculated as described above. These expressions will also include the circulator insertion loss as a transmission factor $T_c$.

Figure 1:
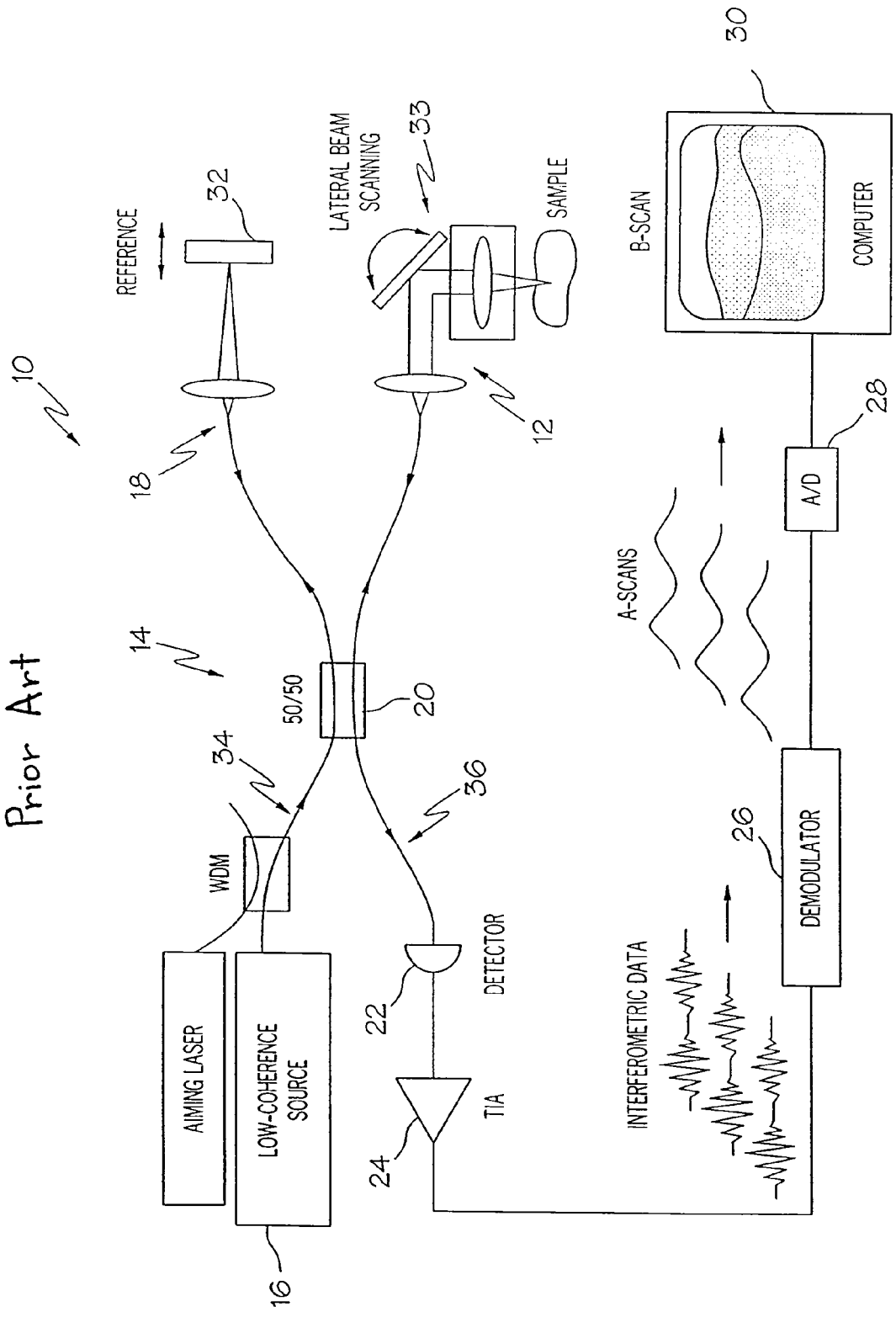
FIG. 1 is a schematic illustration of a traditional OCT system.
Figure 2:
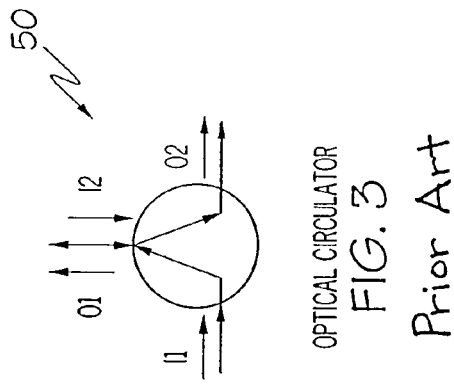
FIG. 2 is a schematic illustration of a reciprocal beamsplitter.

As described earlier, the typical OCT configuration is a standard Michelson interferometer (FIG. 1a). In this case, $P_r = P_0 R_r/4$, $P_s = P_0 R_s/4$, and $P_x = P_0 R_x/4$, where $P_0$ is the power output of the optical source, and $R_r$, $R_s$, and $R_x$ are the power reflectivities of the reference ODL, coherent backscattering from the sample, and the incoherent scattering from the sample arm optics, respectively. From equation (16), this results in:

$$SNR = \frac{\rho^2 P_0^2 R_r R_s/8}{\sigma_{re}^2 + q\rho P_0 (R_r + R_x)B/2 + (RIN)\rho^2 P_0^2 (R_r + R_x)^2 B/16} \quad (18)$$

From inspection of the expressions, it can be seen that receiver noise power is constant, shot noise power is approximately proportional to $R_r$, and excess intensity noise power is approximately proportional to $R_r^2$, while $\langle I_s^2 \rangle$ is proportional to $R_r$. From this, we expect excess photon noise to dominate for high $R_r$, and receiver noise to dominate for very low $R_r$. It is clear that low reference arm reflectivity is required to optimize the standard OCT interferometer, i.e. the reference arm must be attenuated. Again, because it is desirable to use all available optical source power for imaging, this configuration is not optimum.

For the first embodiment, illustrated in FIG. 6, expressions will be derived for the case of a balanced second coupler and balanced differential detection, and for the case of an unbalanced second couple, and a single detector. In the balanced case, for each detector, $P_r = P_0 R_r \alpha T_c^2/2$, $P_s = P_0 R_s (1-\alpha)T_c^2/2$, and $P_x = P_0 R_x (1-\alpha)T_c^2/2$, where $\alpha$ is the splitting ratio of the unbalanced coupler, and $T_c$ is the transmission through the circulator (for 0.7 dB insertion loss, $T_c = 0.85$). More exact expressions would include losses due to optical elements, splices, etc. From equation (17), these expressions result in:

$$SNR = \frac{\rho^2 P_0^2 \alpha(1-\alpha) R_r R_s T_c^4}{\sigma_{re}^2 + q\rho P_0 T_c^2 (R_r \alpha + R_x (1-\alpha))B + (1+V^2)\rho^2 P_0^2 \alpha(1-\alpha) R_r R_x T_c^4 B/2\Delta v} \quad (19)$$

The optimization procedure consists of maximizing this expression for SNR as a function of splitting ratio $\alpha$. The optimum splitting ratio depends on the properties of the optical source, photodetectors, and delay line. An explicit expression for the optimum splitting ratio could by obtained analytically by maximizing the SNR, or alternatively, the modeled SNR could be plotted and the optimum splitting ratio can simply be read from the plot. The embodiment illustrated in FIG. 6 can also be implemented with an unbalanced second coupler and a single detector. In this case, $P_r = P_0 R_r \alpha_1 \alpha_2 T_c^2$, $P_s = P_0 P_s (1-\alpha_1)(1-\alpha_2)T_c^2$, and $P_x = P_0 R_x (1-\alpha_1)(1-\alpha_2)T_c^2$, where $\alpha_1$ is the splitting ratio of the first coupler and $\alpha_2$ is the splitting ratio of the second coupler. From equation (16), the SNR of this configuration as a function of splitting ratio is given by:

$$SNR = \frac{2\rho^2 P_0^2 R_r R_s \alpha_1 \alpha_2 (1-\alpha_1)(1-\alpha_2)T_c^4}{\sigma_{re}^2 + 2q\rho P_0 T_c^2 (R_r \alpha_1 \alpha_2 + R_x (1-\alpha_1)(1-\alpha_2))B + (RIN)\rho^2 P_0^2 T_c^4 (R_r \alpha_1 \alpha_2 + R_x (1-\alpha_1)(1-\alpha_2))^2 B} \quad (20)$$

The embodiment illustrated in FIG. 7 is similar to the embodiment illustrated in FIG. 6, except that a transmissive delay line is used in the reference arm. Consequently, there is no need of a circulator, and no circulator insertion loss associated with the $P_r$ expression. In the balanced detection case, $P_r = P_0 T_r \alpha/2$, $P_s = P_0 R_s (1-\alpha)T_c^2/2$, and $P_x = P_0 R_x (1-\alpha)T_c^2/2$, where $T_r$ is the transmission through the reference delay line. From equation (17), these expressions result in:

$$SNR = \frac{\rho^2 P_0^2 \alpha(1-\alpha) T_r R_s T_c^2}{\sigma_{re}^2 + q\rho P_0 T_c (T_r \alpha + R_x (1-\alpha))B + (1+V^2)\rho^2 P_0^2 \alpha(1-\alpha) T_r R_x T_c^2 B/2\Delta v} \quad (21)$$

The embodiment illustrated in FIG. 7 can also be implemented with an unbalanced second coupler and a single detector. In this case, $P_r = P_0 T_r \alpha_1 \alpha_2$, $P_s = P_0 P_s (1-\alpha_1)(1-\alpha_2)T_c^2$, and $P_x = P_0 R_x (1-\alpha_1)(1-\alpha_2)T_c^2$, where $\alpha_1$ is the splitting ratio of the first coupler and $\alpha_2$ is the splitting ratio of the second coupler. From equation (16), the SNR of this configuration as a function of splitting ratio is given by:

$$SNR = \frac{2\rho^2 P_0^2 T_r R_s \alpha_1 \alpha_2 (1-\alpha_1)(1-\alpha_2)T_c^2}{\sigma_{re}^2 + 2q\rho P_0 T_c (T_r \alpha_1 \alpha_2 + R_x (1-\alpha_1)(1-\alpha_2))B + (RIN)\rho^2 P_0^2 T_c^2 (T_r \alpha_1 \alpha_2 + R_x (1-\alpha_1)(1-\alpha_2))^2 B} \quad (22)$$

In the embodiment illustrated in FIG. 8, a retroreflecting ODL is used without the need for a second optical circulator. In the balanced receiver case, for each detector, $P_r = P_0 R_r \alpha (1-\alpha)/2$, $P_s = P_0 R_s (1-\alpha)T_c^2/2$, and $P_x = P_0 R_x (1-\alpha)T_c^2/2$. From equation (17), these expressions result in:

$$SNR = \frac{\rho^2 P_0^2 \alpha(1-\alpha)^2 R_r R_s T_c^2}{\sigma_{re}^2 + q\rho P_0 (1-\alpha)(R_r \alpha + R_x T_c^2)B + (1+V^2)\rho^2 P_0^2 \alpha(1-\alpha)^2 R_r R_x T_c^2 B/2\Delta v} \quad (23)$$

The embodiment illustrated in FIG. 8 can also be implemented with an unbalanced second coupler and a single detector. In this case, $P_r = P_0 R_r \alpha_1 \alpha_2 (1-\alpha_1)$, $P_s = P_0 R_s (1-\alpha_1)(1-\alpha_2)T_c^2$, and $P_x = P_0 R_x (1-\alpha_1)(1-\alpha_2)T_c^2$. From equation (16), the SNR of this configuration as a function of splitting ratio is given by:

$$SNR = \frac{2\rho^2 P_0^2 R_r R_s \alpha_1 \alpha_2 (1-\alpha_1)^2 (1-\alpha_2)T_c^2}{\sigma_{re}^2 + 2q\rho P_0 (1-\alpha_1)(R_r \alpha_1 \alpha_2 + R_x (1-\alpha_2)T_c^2)B + (RIN)\rho^2 P_0^2 (1-\alpha_1)^2 (R_r \alpha_1 \alpha_2 + R_x (1-\alpha_2)T_c^2)^2 B} \quad (24)$$

The embodiment illustrated in FIG. 9 uses a Michelson interferometer efficiently by introducing an optical circulator into the source arm instead of the sample arm, as in the previous embodiments. This embodiment uses an unbalanced splitter and a single detector. Here, $P_r = P_0 R_r \alpha^2$, $P_s = P_0 P_s (1-\alpha)^2 T_c^2$, and $P_x = P_0 P_x (1-\alpha)^2 T_c^2$, and from equation (16), the SNR of this configuration as a function of splitting ratio is given by:

$$SNR = \frac{2\rho^2 P_0^2 R_r R_s \alpha^2 (1-\alpha_1)^2 T_c^4}{\sigma_{re}^2 + 2q\rho P_0 T_c^2 (R_r \alpha^2 + R_x (1-\alpha_1)^2)B + (RIN)\rho^2 P_0^2 T_c^4 (R_r \alpha^2 + R_x (1-\alpha_1)^2)^2 B}. \quad (25)$$

The embodiment illustrated in FIG. 10 utilizes a balanced receiver. Here, for each detector, $P_r = P_0 R_r T_c^2/4$, $P_s = P_0 R_s$ $T_c^2/4$, and $P_x = P_0 R_s T_c^2/4$, assuming detector d2 is attenuated by an amount equivalent to $T_c$. From equation (17), these expressions result in:

$$SNR = \frac{\rho^2 P_0^2 R_r R_s T_c^4 / 4}{\sigma_{re}^2 + q\rho P_0 T_c^2 (R_r + R_x) B/2 + (1 + V^2)\rho^2 P_0^2 T_c^4 R_r R_x B / 8\Delta v} \quad (26)$$

It must be noted that this embodiment uses a single balanced coupler and therefore there is no optimization required beyond balancing the detectors. This embodiment has the significant advantage that an existing fiber-optic Michelson interferometer OCT system can be easily retrofitted with a circulator in the source arm and a balanced receiver with no need to disturb the rest of the system. We have recently demonstrated this embodiment in a high-speed endoscopic OCT system.

Figure 11:
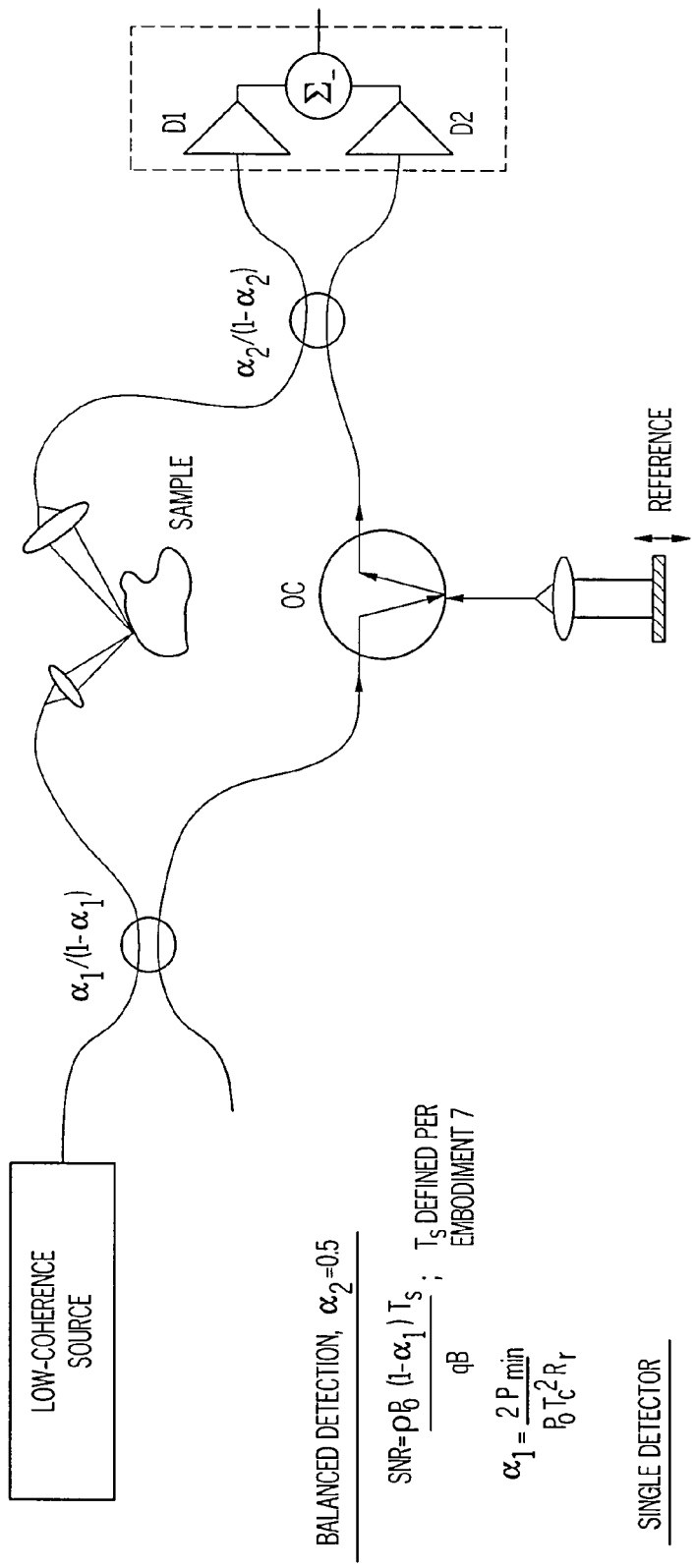
FIG. 11 is a schematic illustration of another interferometer embodiment according to the invention.
Figure 12:
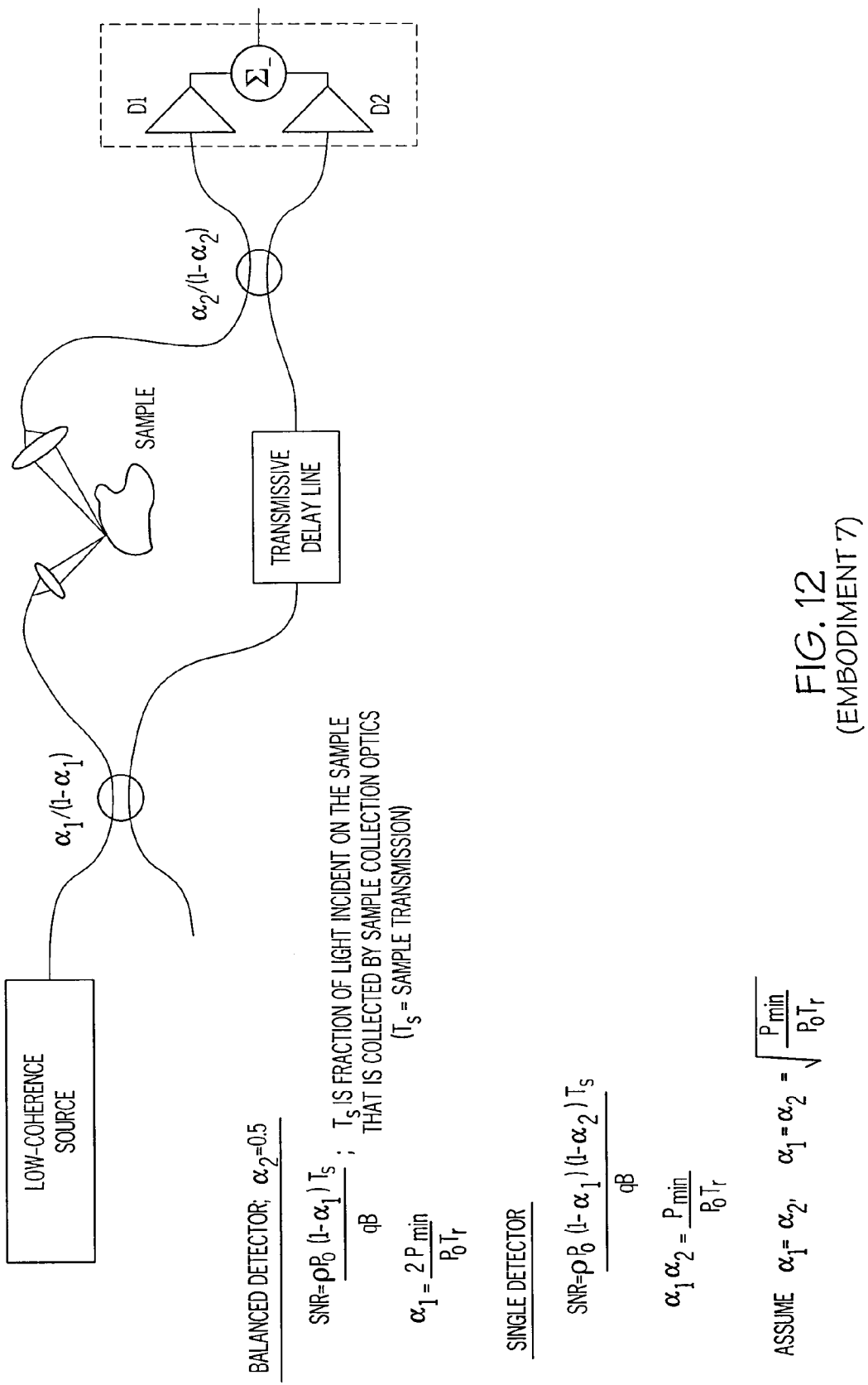
FIG. 12 is a schematic illustration of another interferometer embodiment according to the invention.
Figure 13:
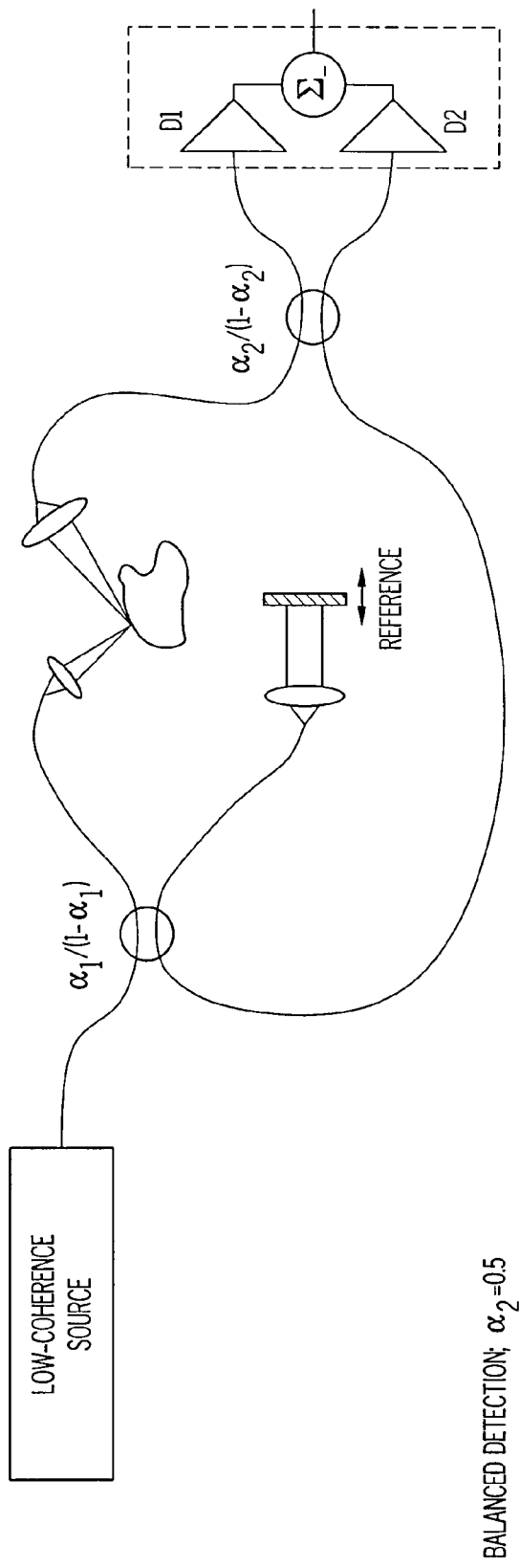
FIG. 13 is a schematic illustration of another interferometer embodiment according to the invention.

There are many practical applications for using OCDR and OCT to image transmissive samples, rather than reflective samples. Here we define transmissive as any sample illumination and collection geometry in which the illumination and collection optics occupy separate optical paths, for example using separate fibers for illumination and collection of light from the sample. The path of light through the sample may be in a straight line, in which case the illumination and collection optics would be lined up along a path aimed directly through the sample. Alternatively, the path of light through the sample may be transmissive in the sense illustrated in FIGS. 11-13, in which there is some angle (other than 0 or 180 degrees) between the illumination and collection optical directions. Although these latter configurations are in some sense reflective geometries, for the purposes of this description we define them as transmissive so long as separate optical paths are used for illumination and collection. In the straight-line geometry (with an angle of 180 degrees between the illumination and collection optics), OCDR and OCT can be used to form images of the internal structure of biological or other materials. In the non-straight line geometry (with any angle other than 0 or 180 degrees between the illumination and collection optics), OCDR and OCT may be used to probe the internal structure of biological or other materials in cases in which it is not convenient to use a retro-reflection geometry (as in embodiments 1-5). There may be other compelling reasons to use an off-axis illumination/collection geometry, for example such geometries may be especially sensitive to internal features of the structure of the sample (e.g., cell nucleus sizing in biological tissues).

We disclose three further embodiments (embodiments 6 through 8, illustrated in FIGS. 11-13, respectively) which are similar in many respects to embodiments 1 through 3, respectively, except that they are designed to accommodate samples which are transmissive rather than reflective.

Embodiment 6

This embodiment is similar in all respects to embodiment 1, except that a transmissive sample is used in the place of the circulator and sample in embodiment 1.

Under the assumption of shot-noise limited detection, the expressions for SNR of this embodiment using dual-balanced and single-detector configurations are given by equations (3) and (5), respectively, under the conditions that $T_c=1$ (since there is no circulator in embodiment 6) and that $R_s$ is interpreted as the transmission of the sample rather than its reflectivity. The optimal splitting ratios for the first unbalanced coupler and for both unbalanced couplers using dual-balanced and single-detector configurations are given by equations (4) and (6), respectively, under these same conditions.

Under the assumption that the more sophisticated signal-to-noise ratio analysis must be used, the expressions for SNR of this embodiment using dual-balanced and single-detector configurations are given by equations (19) and (20), respectively, again under the conditions that $T_c=1$ (since there is no circulator in embodiment 6) and that $R_s$ is interpreted as the transmission of the sample rather than its reflectivity. The procedures for optimizing the splitting ratios for the first unbalanced coupler and for both unbalanced couplers using dual-balanced and single-detector configurations are the same as described for the reflective sample configurations immediately following equations (19) and (20), respectively.

Embodiment 7

This embodiment is similar in all respects to embodiment 2, except that a transmissive sample is used in the place of the circulator and sample in embodiment 1.

Under the assumption of shot-noise limited detection, the expressions for SNR of this embodiment using dual-balanced and single-detector configurations are also given by equations (3) and (5), respectively, under the conditions that $T_c=1$ (since there is no circulator in embodiment 7) and that $R_s$ is interpreted as the transmission of the sample rather than its reflectivity. The optimal splitting ratios for the first unbalanced coupler and for both unbalanced couplers using dual-balanced and single-detector configurations are given by equations (7) and (8), respectively, under these same conditions.

Under the assumption that the more sophisticated signal-to-noise ratio analysis must be used, the expressions for SNR of this embodiment using dual-balanced and single-detector configurations are given by equations (21) and (22), respectively, again under the conditions that $T_c=1$ (since there is no circulator in embodiment 7) and that $R_s$ is interpreted as the transmission of the sample rather than its reflectivity. The procedures for optimizing the splitting ratios for the first unbalanced coupler and for both unbalanced couplers using dual-balanced and single-detector configurations are the same as described for the reflective sample configurations immediately following equations (21) and (22), respectively.

Embodiment 8

This embodiment is similar in all respects to embodiment 3, except that a transmissive sample is used in the place of the circulator and sample in embodiment 3.

Under the assumption of shot-noise limited detection, the expressions for SNR of this embodiment using dual-balanced and single-detector configurations are also given by equations (3) and (5), respectively, under the conditions that $T_c=1$ (since there is no circulator in embodiment 8) and that $R_s$ is interpreted as the transmission of the sample rather than its reflectivity. The optimal splitting ratios for the first unbalanced coupler and for both unbalanced couplers using dual-balanced and single-detector configurations are given by equations (7) (under the assumption that $\alpha_1$ is small) and (8) (under the assumption that both $\alpha_1$ and $\alpha_2$ are small), respectively, under these same conditions.

Under the assumption that the more sophisticated signal-to-noise ratio analysis must be used, the expressions for SNR of this embodiment using dual-balanced and single-detector configurations are given by equations (23) and (24), respectively, again under the conditions that $T_c=1$ (since there is no circulator in embodiment 8) and that $R_s$ is interpreted as the transmission of the sample rather than its reflectivity. The procedures for optimizing the splitting ratios for the first unbalanced coupler and for both unbalanced couplers using dual-balanced and single-detector configurations are the same as described for the reflective sample configurations immediately following equations (23) and (24), respectively.

Although various embodiments and aspects of the invention have been described herein in detail, it is recognized that modifications, improvements, and variations can be made without departing from the spirit and scope of the invention as set forth in the accompanying claims.

What is claimed is:

1. An interferometer for use in an OCDR or OCT imaging system to image a sample, comprising:
    an optical radiation source;
    a nonreciprocal optical element having a first input connected to receive optical radiation from the optical radiation source and a combination first output/second input; and
    a beamsplitter having a first input connected to the combination first output/second input of the nonreciprocal optical element, the beamsplitter having a first output connected for directing optical radiation to a sample to be imaged and for receiving reflected optical radiation from the sample to be imaged, and the beamsplitter having a second output connected for directing optical radiation to a reference delay element and for receiving reflected optical radiation from the reference delay element.

2. Interferometer of claim 1, further comprising:
    an optical radiation detector connected to receive optical radiation from a second output of the non reciprocal optical element.

3. The interferometer of claim 2, wherein the optical radiation detector comprises a first optical radiation detector connected to receive optical radiation from a second output of the non reciprocal optical element and a second optical radiation detector connected to receive optical radiation from a second input of the beamsplitter.

4. interferometer of claim 3, wherein the first optical radiation detector and the second optical radiation detector are connected to form a differential optical radiation detector.

5. The interferometer of claim 3, wherein the first optical radiation detector and the second optical radiation detector are connected to form a differential detector.

6. The interferometer of claim 1, wherein the beamsplitter comprises a balanced beamsplitter.

7. The interferometer of claim 1, wherein the beamsplitter comprises an unbalanced beamsplitter.

8. The interferometer of claim 1, wherein the beamsplitter is an unbalanced beamsplitter that delivers at least 85% of the optical radiation received at the first input to the first output.

9. The interferometer of claim 1, wherein the nonreciprocal optical element comprises an optical circulator.

10. The interferometer of claim 1, further comprising a beamsplitter connected between the optical radiation source and the nonreciprocal optical element.

11. The interferometer of claim 1, further comprising one or more beamsplitters connected between the optical radiation source and the nonreciprocal optical element.

12. An interferometer system for imaging a sample at a sample location, comprising:
    an optical radiation source, a beamsplitter, and an optical circulator connected between the optical radiation source and the beamsplitter for transmitting optical radiation from the optical radiation source through the optical circulator to a sample location, an output of the optical circulator being connected to direct optical radiation to an optical radiation detector.

13. The interferometer of claim 12, wherein the optical circulator comprises a Faraday rotator and a polarizing beamsplitter.

14. The interferometer of claim 12, wherein the beamsplitter includes a first output connected to direct light to the sample location and a second output connected to direct light to a reference location.

15. The interferometer of claim 12, further comprising a beamsplitter connected between the optical radiation source and the nonreciprocal optical element.

16. The interferometer of claim 12, wherein the optical detector comprises first and second optical detectors, the first optical detector connected to the optical circulator and the second optical detector coupled to the beamsplitter.

17. An interferometer system for imaging a sample at a sample location, the interferometer comprising:
    an optical radiation source, a nonreciprocal optical element, a beamsplitter and an optical detector; a first optical path extending from the optical radiation source, through a first portion of the nonreciprocal optical element, through the beamsplitter to a sample location, and from the sample location through the beamsplitter and a second portion of the nonreciprocal optical element to the optical detector.

18. The interferometer of claim 17, wherein the optical detector comprises first and second optical detectors, the first optical detector positioned at the end of the first optical path, the interferometer further comprising:
    a second optical path extending from the optical radiation source, through the first portion of the nonreciprocal optical element and through the beamsplitter to a reference location, and from the reference location to the second optical detector.

19. The interferometer of claim 17, further comprising:
    a second optical path extending from the optical radiation source, through the first portion of the nonreciprocal optical element to a reference location, from the reference location through the second portion of the nonreciprocal optical element to the optical detector.

20. The interferometer of claim 17, wherein the nonreciprocal optical element is an optical circulator.

* * * * *